(12) United States Patent
Iwata et al.

(10) Patent No.: US 9,447,065 B2
(45) Date of Patent: Sep. 20, 2016

(54) PHARMACEUTICAL COMPOSITION

(71) Applicant: RaQualia Pharma Inc., Aichi (JP)

(72) Inventors: Yasuhiro Iwata, Aichi (JP); Kaoru Shimada, Aichi (JP); Yoshiyuki Okumura, Aichi (JP); Mayumi Kashino, Aichi (JP); Hiromitsu Yoshida, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 237 days.

(21) Appl. No.: 14/351,190

(22) PCT Filed: Oct. 18, 2012

(86) PCT No.: PCT/JP2012/076899
§ 371 (c)(1),
(2) Date: Apr. 11, 2014

(87) PCT Pub. No.: WO2013/058303
PCT Pub. Date: Apr. 25, 2013

(65) Prior Publication Data
US 2014/0256804 A1  Sep. 11, 2014

(30) Foreign Application Priority Data
Oct. 18, 2011 (JP) .................................. 2011-228846

(51) Int. Cl.
| | |
|---|---|
| *A61K 31/352* | (2006.01) |
| *C07D 311/58* | (2006.01) |
| *A61K 9/16* | (2006.01) |
| *A61K 9/20* | (2006.01) |
| *A61K 47/48* | (2006.01) |
| *C08B 37/16* | (2006.01) |
| *C08L 5/16* | (2006.01) |
| *B82Y 5/00* | (2011.01) |

(52) U.S. Cl.
CPC ........... *C07D 311/58* (2013.01); *A61K 9/1617* (2013.01); *A61K 9/1652* (2013.01); *A61K 9/205* (2013.01); *A61K 9/2013* (2013.01); *A61K 31/352* (2013.01); *A61K 47/48969* (2013.01); *B82Y 5/00* (2013.01); *C08B 37/0015* (2013.01); *C08L 5/16* (2013.01); *A61K 9/1623* (2013.01); *A61K 9/2018* (2013.01); *A61K 9/2054* (2013.01)

(58) Field of Classification Search
CPC ............................ A61K 31/352; C07D 311/58
USPC .......................................... 514/456; 549/405
See application file for complete search history.

(56) References Cited

U.S. PATENT DOCUMENTS

| | | | |
|---|---|---|---|
| 6,034,256 | A | 3/2000 | Carter et al. |
| 7,109,211 | B2 | 9/2006 | Carter et al. |
| 2003/0105141 | A1 | 6/2003 | Gao et al. |
| 2005/0042291 | A1 | 2/2005 | Hawley et al. |

FOREIGN PATENT DOCUMENTS

| | | |
|---|---|---|
| JP | 2002-511062 A | 4/2002 |
| JP | 2007-511062 A | 4/2007 |
| JP | 2007-527394 A | 9/2007 |
| JP | 2008-542260 A | 11/2008 |
| JP | 4577534 B2 | 11/2010 |
| WO | 2005084654 A2 | 9/2005 |
| WO | 2006040672 A1 | 4/2006 |
| WO | 2006126214 A3 | 11/2006 |

OTHER PUBLICATIONS

Partial Supplementary European Search Report issued Feb. 18, 2015 in corresponding European application No. 12841913.2 (7 pages).
International Preliminary Report on Patentability issued in PCT/JP2012/076899 mailed on May 1, 2014 (9 pages).
International Search Report issued in PCT/JP2012/076899 mailed on Nov. 27, 2012 (8 pages).
"Rofecoxib-[Beta]-cyclodextrin inclusion complex for solubility enhancement" Rawat, S. et al; Pharmazie vol. 58 No. 9 pp. 639-641 (2003) (3 pages).
"Cyclodextrin/imatinib complexation: Binding mode and charge dependent stabilities" Beni, S. et al, European Journal of Pharmaceutical Sciences vol. 30 pp. 167-174 (2007) (8 pages).
Extended European Search Report in corresponding European Application No. 12841913 dated Jun. 1, 2015 (11 pages).
Office Action issued in corresponding Japanese Application No. 2013-539678, mailed on Jul. 19, 2016 (4 pages).

*Primary Examiner* — Raymond Henley, III
(74) *Attorney, Agent, or Firm* — Osha Liang LLP

(57) ABSTRACT

The present invention provides a pharmaceutical composition which prevents from decreasing the blood exposure of the third generation coxib-drugs, a process for preparing the said pharmaceutical composition and its use.
It has been founded in this invention that adding a basic amine or a basic amino acid, or a cyclodextrin to the third generation coxib-drug can afford a pharmaceutical composition which can prevent from decreasing the blood exposure, AUC and bioavailability. The pharmaceutical composition of the present invention has also good stability, which is useful for drugs. Namely, the technological thought that adding a basic amine or a basic amino acid, or a cyclodextrin to the third generation coxib-drug can prevent from decreasing the blood exposure, AUC and bioavailability has been established in this invention.

18 Claims, 3 Drawing Sheets

PHARMACEUTICAL COMPOSITION

TECHNICAL FIELD

This invention relates to compositions containing a compound represented by the formula (I)

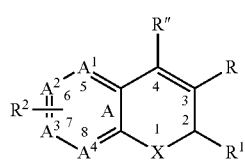

(I)

(the descriptors in the formula are described later)
or a pharmaceutically-acceptable salt thereof, a process for preparing the said pharmaceutical composition, and its use for treating cyclooxygenase-2 mediated diseases.

BACKGROUND ART

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, which limit their therapeutic potential. An alternative to NSAIDs is the use of corticosteroids, which have even more drastic side effects, especially when long term therapy is involved.

NSAIDs prevent the production of prostaglandins by inhibiting enzymes in the human arachidonic acid/prostaglandin pathway, including the enzyme cyclooxygenase (COX). The expression of cyclooxygenase-2 (COX-2) is specifically induced in the pathological conditions such as inflammation, pain, and cancer, and is involved in the generation and maintenance of these conditions. According to the line, a series of drugs called coxibs such as celecoxib, rofecoxib, valdecoxib, parecoxib, and etoricoxib have been developed.

The benzopyran, dihydroquinoline, benzothiopyran and dihydronapthalene derivatives, represented by the formula (I) in this invention are disclosed in the patent literature 1, and preferably selectively inhibit cyclooxygenase-2 over cyclooxygenase-1. Among them, the benzopyran derivative, for example, affords more potent analgesia and more rapid onset of effect than ibuprofen which is the first choice among the conventional drugs. Furthermore it has been confirmed in the preclinical studies that the benzopyran derivatives have lower renal problem which are a matter of concern in conventional COX-2 inhibitors and NSAIDs.

Coxib-drugs are useful for the treatment of diseases mediated by cyclooxygenase-2, such as inflammation, pain, cancer, fever, osteoarthritis, rheumatoid arthritis, migraine, neurodegenerative diseases, cardiovascular disease, osteoporosis, asthma, lupus and psoriasis, dysmenorrhea, premature labor, glaucoma, gout, ankylosing spondylitis, bursitis, heat burn, sprain, and contusion.

In general, active ingredients involved in coxib-drugs have a sulfonamide group, whereas the compound of the formula (I) is a unique chemical structure, which has neither sulfonamide group nor alkylsulfonyl group but has a carboxylic acid group. (Hereafter in the present specification, such coxib-drugs or coxib-compounds, which have neither a sulfonamide group nor an alkylsulfonyl group but have a carboxylic acid group, are called third generation coxib-drugs or coxib-compounds.) As the compound of the formula (I) has a carboxylic acid group in its chemical structure, the solubility in the low pH field is inferior to that in the neutral or basic condition. Therefore, depending on gastric residence time, the solubility problem may cause the precipitation of the compound followed by insufficient absorption, resulting in decreasing blood concentration and bioavailability. These adverse events are observed in common with third generation coxib-drugs or coxib-compounds defined in the present specification.

Actually, results of clinical studies are obtained that when Compound A (defined below) was administered with the standard tablet formulation, the initial blood concentration after the administration was low comparing with administered with the solution (OPC, Oral Powder Constitution: a solution simply dissolved the active ingredient).

From this background, it has been investigated that a method for providing a pharmaceutical composition of a cyclooxygenase-2 inhibitor in which the stability and/or solubility are improved. Namely, the patent literature 2 discloses "a novel injectable pharmaceutical composition comprising at least one COX-II inhibitor or NSAID or COX/LOX inhibitor or its tautomeric forms, or its analogues, isomers, polymorphs, solvates, prodrugs, or salts or thereof as active ingredient from 0.1% to 80% w/v and a solvent system comprising a mixture of glycols from 1% to 80% v/v; optionally with other pharmaceutically acceptable excipients" and also discloses "a composition according to claim 1, wherein the said composition additionally comprises at least one alkalizing agent from 0.2% to 60% v/v". However, this is a pharmaceutical formulation as an injectable drug, and therefore an effectual means as an oral formulation which solves these issues has been desired.

As a method for keeping the basicity of the third generation coxib-drug, a method of adding a basic alkaline-earth metal salt such as calcium carbonate, calcium hydroxide, magnesium carbonate, magnesium silicate, and magnesium aluminate as an excipient was tried, but when adding such a basic alkaline-earth metal salt to Compound A, no preferable results were obtained.

CITATION LIST

Patent Literature

{PL 1} JP Patent No. 4577534
{PL 2} Japanese Unexamined Patent Application Publication (Translation of PCT Application) No. 2008-542260 pamphlet

SUMMARY OF INVENTION

Problems to be Resolved by the Invention

It is an object of the present invention to provide a pharmaceutical composition containing as an active substance a coxib-drug which exerts an excellent stability while avoiding the aforementioned disadvantages. It is also an object to provide a process for preparing the said pharmaceutical composition and its use.

Means for Solving the Problem

Taking the above circumstances into consideration, after an exhaustive and careful study aiming to prevent from decreasing the blood exposure of coxib-drugs represented by the formula (I), surprisingly the inventors of the present invention have managed to find out that adding a basic amine or basic amino acid to the compound of formula (I), or forming cyclodextrin inclusion complex with the compound of formula (I) can afford a pharmaceutical composition which can prevent from decreasing the blood exposure. The pharmaceutical composition of the present invention has also good stability, which is useful for drugs. An ingredient, which does not give a bad influence over the stability, can be incorporated in the pharmaceutical composition of the present invention. As mentioned in the background art, though there is a technology of injectable drug in the conventional arts, there is no example of oral formulation which gives effective solution of aforementioned disadvantages. The inventors of the present invention have established the technological thought that adding a basic amine or basic amino acid to the coxib-compound, or forming cyclodextrin inclusion complex with the coxib-compound can prevent from decreasing the blood concentration, AUC (area under the blood concentration curve), and bioavailability, and finally completed the invention.

More specifically, this invention discloses:
[1] A pharmaceutical composition comprising a third-generation coxib-compound or a pharmaceutically acceptable salt thereof, wherein the pharmaceutical composition contains at least one basic amine or basic amino acid, or at least one cyclodextrin in the range of 0.5% (weight/whole pharmaceutical composition weight) or more;
[2] The pharmaceutical composition according to [1], wherein at least one basic amine or basic amino acid, or at least one cyclodextrin is contained in the range of 5 to 70% (weight/whole pharmaceutical composition weight);
[3] The pharmaceutical composition according to [1] or [2], wherein the third-generation coxib-compound is a compound represented by the formula (I):

{Chem. 2}

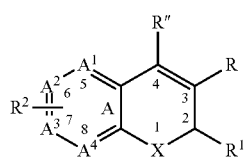
(I)

wherein X is selected from O, S and $NR^a$;
wherein $R^a$ is selected from hydrido, $C_1$-$C_3$-alkyl, (optionally substituted phenyl)-methyl, and phenylmethyl; wherein the phenyl ring is substituted by 1 to 3 substituents independently selected from $C_1$-$C_6$-alkyl, hydroxyl, halo, $C_1$-$C_6$-haloalkyl, nitro, cyano, $C_1$-$C_6$-alkoxy and $C_1$-$C_6$-alkylamino;
wherein R is carboxyl;
wherein R" is selected from hydrido and $C_2$-$C_6$-alkenyl;
wherein $R^1$ is selected from $C_1$-$C_3$-perfluoroalkyl, chloro, $C_1$-$C_6$-alkylthio, nitro, cyano and cyano-$C_1$-$C_3$-alkyl;

wherein $R^2$ is one or more radicals independently selected from hydrido; halo; $C_1$-$C_6$-alkyl; $C_2$-$C_6$-alkenyl; $C_2$-$C_6$-alkynyl; halo-$C_2$-$C_6$-alkynyl; phenyl-$C_1$-$C_6$-alkyl; phenyl-$C_2$-$C_6$-alkenyl; phenyl-$C_2$-$C_6$-alkenyl; $C_1$-$C_3$-alkoxy; methylenedioxy; $C_1$-$C_3$-alkoxy-$C_1$-$C_3$-alkyl; $C_1$-$C_3$-alkylthio; $C_1$-$C_3$-alkylsulfinyl; phenyloxy; phenylthio; phenylsulfinyl; $C_1$-$C_3$-haloalkyl-$C_1$-$C_3$-hydroxyalkyl; phenyl-$C_1$-$C_3$-alkoxy-$C_1$-$C_3$-alkyl; $C_1$-$C_3$-haloalkyl; $C_1$-$C_3$-haloalkoxy; $C_1$-$C_3$-haloalkylthio; $C_1$-$C_3$-hydroxyalkyl; hydroxyimino-$C_1$-$C_3$-alkyl; $C_1$-$C_6$-alkylamino; nitro; cyano; amino; aminosulfonyl; N—($C_1$-$C_6$-alkyl)aminosulfonyl; N-arylaminosulfonyl; N-heteroarylaminosulfonyl; N-(phenyl-$C_1$-$C_6$-alkyl)aminosulfonyl; N-(heteroaryl-$C_1$-$C_6$-alkyl)aminosulfonyl; phenyl-$C_1$-$C_3$-alkylsulfonyl; 5- to 8-membered heterocyclylsulfonyl; $C_1$-$C_6$-alkylsulfonyl; phenyl; optionally substituted phenyl substituted by one or more radicals selected from chloro, fluoro, bromo, methoxy, methylthio and methylthiosulfonyl; 5- to 9-membered heteroaryl; chloro substituted thienyl; phenyl-$C_1$-$C_6$-alkylcarbonyl; phenylcarbonyl; 4-chlorophenylcarbonyl; 4-hydroxyphenylcarbonyl; 4-trifluoromethylphenylcarbonyl; 4-methoxyphenylcarbonyl; aminocarbonyl; formyl; and $C_1$-$C_6$-alkylcarbonyl;
wherein the A ring atoms $A^1$, $A^2$, $A^3$ are carbon and $A^4$ is carbon or nitrogen, or wherein $R^2$ together with ring A forms a naphthyl, benzofurylphenyl, or quinolyl radical; or an isomer thereof;
[4] The pharmaceutical composition according to any one of [1] to [3], wherein the compound of the formula (I) is selected from the group consisting of
6-chloro-2-trifluoromethyl-2H-1-benzopyran-3-carboxylic acid;
6-chloro-7-methyl-2-trifluoromethyl-2H-1-benzopyran-3-carboxylic acid;
8-(1-methylethyl)-2-trifluoromethyl-2H-1-benzopyran-3-carboxylic acid;
6-chloro-7-(1,1-dimethylethyl)-2-trifluoromethyl-2H-1-benzopyran-3-carboxylic acid;
6-chloro-8-(1-methylethyl)-2-trifluoromethyl-2H-1-benzopyran-3-carboxylic acid;
2-trifluoromethyl-3H-naphthopyran-3-carboxylic acid;
7-(1,1-dimethylethyl)-2-trifluoromethyl-2H-1-benzopyran-3-carboxylic acid;
6-bromo-2-trifluoromethyl-2H-1-benzopyran-3-carboxylic acid;
8-chloro-2-trifluoromethyl-2H-1-benzopyran-3-carboxylic acid;
6-trifluoromethoxy-2-trifluoromethyl-2H-1-benzopyran-3-carboxylic acid;
5,7-dichloro-2-trifluoromethyl-2H-1-benzopyran-3-carboxylic acid;
8-phenyl-2-trifluoromethyl-2H-1-benzopyran-3-carboxylic acid;
7,8-dimethyl-2-trifluoromethyl-2H-1-benzopyran-3-carboxylic acid;
6,8-bis(dimethylethyl)-2-trifluoromethyl-2H-1-benzopyran-3-carboxylic acid;
7-(1-methylethyl)-2-trifluoromethyl-2H-1-benzopyran-3-carboxylic acid;
7-phenyl-2-trifluoromethyl-2H-1-benzopyran-3-carboxylic acid;
6-chloro-7-ethyl-2-trifluoromethyl-2H-1-benzopyran-3-carboxylic acid;
6-chloro-8-ethyl-2-trifluoromethyl-2H-1-benzopyran-3-carboxylic acid;
6-chloro-7-phenyl-2-trifluoromethyl-2H-1-benzopyran-3-carboxylic acid;

6,7-dichloro-2-trifluoromethyl-2H-1-benzopyran-3-carboxylic acid;
6,8-dichloro-2-trifluoromethyl-2H-1-benzopyran-3-carboxylic acid;
2-trifluoromethyl-3H-naphtho[2,1-b]pyran-3-carboxylic acid;
6-chloro-8-methyl-2-trifluoromethyl-2H-1-benzopyran-3-carboxylic acid;
8-chloro-6-methyl-2-trifluoromethyl-2H-1-benzopyran-3-carboxylic acid;
8-chloro-6-methoxy-2-trifluoromethyl-2H-1-benzopyran-3-carboxylic acid;
6-bromo-8-chloro-2-trifluoromethyl-2H-1-benzopyran-3-carboxylic acid;
8-bromo-6-fluoro-2-trifluoromethyl-2H-1-benzopyran-3-carboxylic acid;
8-bromo-6-methyl-2-trifluoromethyl-2H-1-benzopyran-3-carboxylic acid;
8-bromo-5-fluoro-2-trifluoromethyl-2H-1-benzopyran-3-carboxylic acid;
6-chloro-8-fluoro-2-trifluoromethyl-2H-1-benzopyran-3-carboxylic acid;
6-bromo-8-methoxy-2-trifluoromethyl-2H-1-benzopyran-3-carboxylic acid;
6-[[(phenylmethyl)amino]sulfonyl]-2-trifluoromethyl-2H-1-benzopyran-3-carboxylic acid;
6-[(dimethylamino)sulfonyl]-2-trifluoromethyl-2H-1-benzopyran-3-carboxylic acid;
6-[(methylamino)sulfonyl]-2-trifluoromethyl-2H-1-benzopyran-3-carboxylic acid;
6-[(4-morpholino)sulfonyl]-2-trifluoromethyl-2H-1-benzopyran-3-carboxylic acid;
6-[(1,1-dimethylethyl)aminosulfonyl]-2-trifluoromethyl-2H-1-benzopyran-3-carboxylic acid;
6-[(2-methylpropyl)aminosulfonyl]-2-trifluoromethyl-2H-1-benzopyran-3-carboxylic acid;
6-methylsulfonyl-2-trifluoromethyl-2H-1-benzopyran-3-carboxylic acid;
8-chloro-6-[[(phenylmethyl)amino]sulfonyl]-2-trifluoromethyl-2H-1-benzopyran-3-carboxylic acid;
6-phenylacetyl-2-trifluoromethyl-2H-1-benzopyran-3-carboxylic acid;
6,8-dibromo-2-trifluoromethyl-2H-1-benzopyran-3-carboxylic acid;
8-chloro-5,6-dimethyl-2-trifluoromethyl-2H-1-benzopyran-3-carboxylic acid;
6,8-dichloro-(S)-2-trifluoromethyl-2H-1-benzopyran-3-carboxylic acid;
6-benzylsulfonyl-2-trifluoromethyl-2H-1-benzopyran-3-carboxylic acid;
6-[[N-(2-furylmethyl)amino]sulfonyl]-2-trifluoromethyl-2H-1-benzopyran-3-carboxylic acid;
6-[[N-(2-phenylethyl)amino]sulfonyl]-2-trifluoromethyl-2H-1-benzopyran-3-carboxylic acid;
6-iodo-2-trifluoromethyl-2H-1-benzopyran-3-carboxylic acid;
7-(1,1-dimethylethyl)-2-pentafluoroethyl-2H-1-benzopyran-3-carboxylic acid; and
6-chloro-2-trifluoromethyl-2H-1-benzothiopyran-3-carboxylic acid;
or an isomer thereof;

[5] The pharmaceutical composition according to any one of [1] to [3], wherein the compound of the formula (I) is selected from the group consisting of
6-nitro-2-trifluoromethyl-2H-1-benzopyran-3-carboxylic acid;
6-chloro-8-methyl-2-trifluoromethyl-2H-1-benzopyran-3-carboxylic acid;
(S)-6-chloro-7-(1,1-dimethylethyl)-2-trifluoromethyl-2H-1-benzopyran-3-carboxylic acid (This compound may be called compound A through the present specification);
2-trifluoromethyl-2H-naphtho[2,3-b]pyran-3-carboxylic acid;
6-chloro-7-(4-nitrophenoxy)-2-trifluoromethyl-2H-1-benzopyran-3-carboxylic acid;
(S)-6,8-dichloro-2-trifluoromethyl-2H-1-benzopyran-3-carboxylic acid;
6-chloro-2-trifluoromethyl-4-phenyl-2H-1-benzopyran-3-carboxylic acid;
6-(4-hydroxybenzoyl)-2-trifluoromethyl-2H-1-benzopyran-3-carboxylic acid;
2-(trifluoromethyl)-6-[(trifluoromethyl)thio]-2H-1-benzothiopyran-3-carboxylic acid;
6,8-dichloro-2-trifluoromethyl-2H-1-benzothiopyran-3-carboxylic acid;
6-(1,1-dimethylethyl)-2-trifluoromethyl-2H-1-benzothiopyran-3-carboxylic acid;
6,7-difluoro-1,2-dihydro-2-trifluoromethyl-3-quinolinecarboxylic acid;
6-chloro-1,2-dihydro-1-methyl-2-trifluoromethyl-3-quinolinecarboxylic acid;
6-chloro-2-trifluoromethyl-1,2-dihydro[1,8]naphthyridin-3-carboxylic acid; and
(S)-6-chloro-1,2-dihydro-2-trifluoromethyl-3-quinolinecarboxylic acid or an isomer thereof;

[6] The pharmaceutical composition according to any one of [1] to [5], wherein the basic amine or the basic amino acid is tromethamine, triethanolamine, diethanolamine, monoethanolamine, glucosamine, galactosamine, fructosamine, meglumine, N-ethyl glucamine, lysine, arginine, histidine, tryptophan or ornithine; and
the cyclodextrin is β-cyclodextrin, hydroxypropyl-β-cyclodextrin, or sodium sulfobutylether-β-cyclodextrin (SBECD);

[7] The pharmaceutical composition according to any one of [1] to [6], wherein the basic amine or the basic amino acid is tromethamine, meglumine, lysine, or arginine; and
the cyclodextrin is β-cyclodextrin or hydroxypropyl-β-cyclodextrin;

[8] A process for preparing a pharmaceutical composition, as defined in any one of [1] to [7], wherein the process comprises a step for combining a compound of the formula (I) or an isomer thereof, or a pharmaceutically acceptable salt thereof; and
a basic amine or a basic amino acid, or a cyclodextrin;

[9] The process for preparing a pharmaceutical composition, as defined in any one of [1] to [7], wherein the process comprises combining a compound of the formula (I) or an isomer thereof, or a pharmaceutically acceptable salt thereof; and
a basic amine or a basic amino acid, or a cyclodextrin;
with at least one carrier;
and subjecting the combination to grinding or milling, or granulation;

[10] The process according to [8] or [9], wherein the process further comprises compressing the pharmaceutical composition into a solid dosage form;

[11] A use of a pharmaceutical composition, as defined in any one of [1] to [7] in the manufacture of a medicament for treating and/or preventing a patient suffering from a disease mediated by cyclooxygenase-2; and

[12] The use according to [11], wherein the disease is one or more diseases selected from the group consisting of fever, osteoarthritis, rheumatoid arthritis, migraine, neurodegenerative diseases, cardiovascular diseases, osteoporosis, asthma, lupus and psoriasis, dysmenorrhea, premature labor, glaucoma, gout, ankylosing spondylitis, bursitis, heat burn, sprain, and contusion.

In terms of pharmaceutically-acceptable salts of the third-generation coxib-compound represented by the formula (I), the nature of the salt is not critical, provided that it is pharmaceutically-acceptable.

Pharmaceutically-acceptable acid addition salts of the third-generation coxib-compound represented in the formula (I) can be prepared from an inorganic acid or from an organic acid.

Examples of such inorganic acids are hydrochloric, hydrobromic, hydroiodic, nitric, carbonic, sulfuric and phosphoric acid.

Examples of such organic acids are selected from aliphatic, cycloaliphatic, aromatic, araliphatic, heterocyclic, carboxylic and sulfonic classes of organic acids, which are exemplified by formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, alginic, β-hydroxybutyric, galactaric and galacturonic acid.

Suitable pharmaceutically-acceptable base addition salts of the third-generation coxib-compounds represented by the formula (I) include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine.

All of these salts may be prepared by the conventional means from the corresponding the third-generation coxib-compound represented by the formula (I) and the appropriate acid or base.

Effect of the Invention

The present invention provide a pharmaceutical composition which can prevent from decreasing the blood concentration, AUC, and bioavailability; wherein the pharmaceutical composition has a coxib-compound with cyclooxygenase-2 inhibitory activity as an active pharmaceutical ingredient and incorporated a basic amine, basic amino acid or cyclodextrin. The pharmaceutical composition has also good stability, which is useful for drugs.

Figure 1:
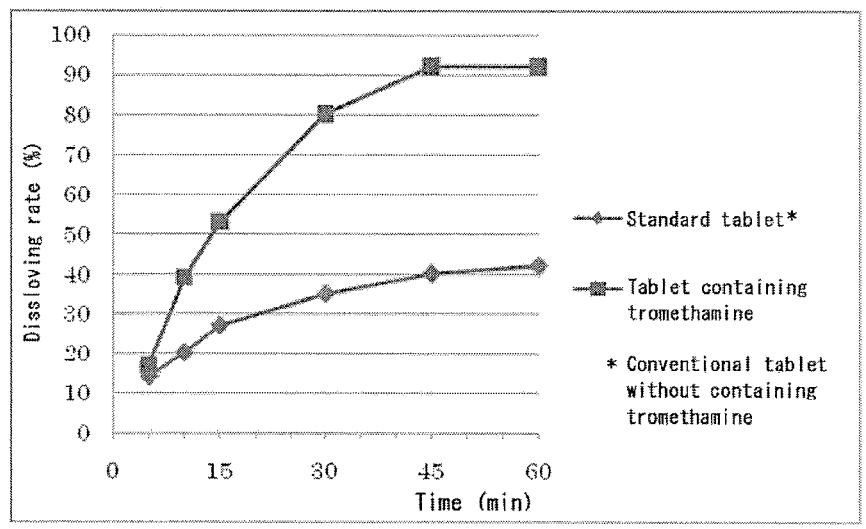
FIG. 1 A graph showing each dissolution amount over time in a tablet of Compound A containing tromethamine which is prepared by the manufacturing process 3 in example 1, and a standard tablet which is prepared by the manufacturing process 2 in comparative example 2. As described in table 10 and table 11, the standard tablet, has a tablet formulation using excipient widely used.

DETAILED DESCRIPTION OF THE INVENTION (Third Generation Coxib-Drug)

A third generation coxib-drug of the present invention includes a pharmaceutically-acceptable salt thereof, an optical isomer and a mixture of their isomers, a solvate, a crystal polymorph, and the like.

A third generation coxib-drug is commercially available or can be prepared by a method known per se.

As used in compounds represented by the formula (I), the term "alkyl" as a group or part of a group e.g. alkoxy or hydroxyalkyl refers to a straight or branched alkyl group in all isomeric forms.

The term "$C_1$-$C_6$ alkyl" refers to an alkyl group, as represented by the formula (I), containing at least 1, and at most 6 carbon atoms. Examples of such alkyl groups include methyl, ethyl, propyl, iso-propyl, n-butyl, iso-butyl, sec-butyl, tert-butyl and the like.

The term "$C_1$-$C_6$ alkenyl" refers to an alkenyl group, as represented by the formula (I), containing at least 1, and at most 6 carbon atoms. Examples of such alkenyl groups include vinyl, 1-propenyl, allyl, 1-butenyl, 2-butenyl, 3-butenyl, pentenyl, hexenyl and the like.

The term "$C_2$-$C_6$ alkynyl", refers to an alkynyl group, as represented by the formula (I), containing at least 2, and at most 6 carbon atoms. Examples of such alkynyl groups include ethynyl, 1-propynyl, 2-propynyl, 1-butynyl, 3-butynyl, pentynyl, hexynyl and the like.

As represented by the formula (I), the term "halogen" refers to fluorine (F), chlorine (Cl), bromine (Br), or iodine (I) and the term "halo" refers to the halogen: fluoro (—F), chloro (—Cl), bromo (—Br) and iodo (—I).

As the term "heteroaryl" in a heteroaryl, 5- to 8-membered heterocyclyl and 5- to 9-membered heteroaryl in the definition of the formula (I), 5- to 6-membered heteroring containing one to three selected from O, N, and S, exemplified by furyl, thienyl, pyridyl, thiazolyl and the like are preferable.

For example, the third coxib-compounds are described in the patent literature 1, JP Patent No. 4577534, etc.

The amount of the third generation coxib-compound contained in a pharmaceutical composition for treating circulatory system diseases according to the present invention is not specifically restricted, however, the dose preferably should be sufficient to treat, ameliorate, or reduce the symptoms associated with the circulatory system disease. The dosage of a pharmaceutical composition for treating circulatory system diseases according to the present invention will depend on the method of use, the age, sex, and condition of the patient. For example, about 1 mg, to 1000 mg of the third generation coxib-compound may be contained in a dosage form. Preferably, about 5 mg, to 500 mg of the third generation coxib-compound may be contained there.

(The Process for Preparing a Pharmaceutical Composition)

The pharmaceutical composition of the present invention may be prepared by any conventional means such as, but not limited to, wet or dry granulation and direct compression.

The process for preparing the pharmaceutical composition of the present invention is characterized by containing a process for combining a basic amine or a basic amino acid, or cyclodextrin with an active pharmaceutical ingredient.

In a direct compression process, the process for preparing a pharmaceutical composition comprises combining a basic amine or a basic amino acid, or cyclodextrin and at least one carrier with an active pharmaceutical ingredient, wherein the carrier is intimately admixed with a basic amine or a basic amino acid, or cyclodextrin. Optionally, one or more other excipients are added to the pharmaceutical composition and the resulting combination is compressed into a solid pharmaceutical composition such as tablets, pills, granules, etc. Preferably, the solid pharmaceutical composition is compressed into a tablet.

In a similar way to the direct compression process, a wet granulation process comprises adding and kneading an appropriate amount of water to the pharmaceutical composition to be formulated and through a further suitable process. The granulated pharmaceutical composition is dried under a suitable condition, and is subject to compression molding to tablet etc after particle size regulation.

Then in a similar way to the direct compression process, a dry granulation process comprises compression molding which comprises compressing a pharmaceutical composition to be formulated to the form of plates with a suitable compressor, crushing the resulting plate with a grinder mill, successively regulating a particle size, and then compression molding to tablet etc.

A basic amine, a basic amino acid, and a cyclodextrin of the present invention are commercially available.

The basic amine (for example, amine such as tromethamine, triethanolamine, diethanolamine, monoethanolamine and the like, or amino sugar such as glucosamine, galactosamine, fructosamine, meglumine, N-ethyl-glucamine, and the like), or the basic amino acid (for example, lysine, arginine, histidine, tryptophan, ornithine, and the like) may be used alone or in a combination of two or more kinds thereof. In a similar manner, the cyclodextrin (for example, β-cyclodextrin, hydroxypropyl-β-cyclodextrin, sulfobutylether-β-cyclodextrin sodium (SBECD), and the like) may be also used alone or in a combination of two or more kinds thereof. These basic amines or basic amino acids, or cyclodextrins are added to the active pharmaceutical ingredient in the form of a liquid state, a solid state, or a suspension state.

In the oral pharmaceutical composition of the present invention obtained by adding a basic amine or a basic amino acid, or a cyclodextrin, coxib-compound is generally ranged from about 1 to 60% (w/w) in the said composition. More preferably that is from 10 to 50% (w/w). The basic amine, the basic amino acid, or the cyclodextrin is not limited as long as no trouble in the formulation, but is in the range of 0.5% (w/w) or more in the said pharmaceutical composition. More preferably that is in the range of 0.5 to 70% (w/w). The amount of the basic amine or the basic amino acid, or the cyclodextrin is in the range of 10 to 50% (w/w).

The pharmaceutical composition of the invention may take any form but it is preferably a solid composition. More preferably, the pharmaceutical composition of the invention is compressed to solid composition by molding (e.g. granulation and pressurization). Suitable solid dosage forms include, but are not limited to, tablets, pill, granules, capsules, powders, and sachets, and the like. Particularly tablets are preferable.

When the pharmaceutical composition is a solid dosage form, the dosage form can be produced by incorporating a basic amine or a basic amino acid, or a cyclodextrin into the active ingredient, followed by subjecting the mixture to molding. The incorporation is conducted by a method conventionally employed in the field of pharmaceutical preparations, such as mixing, kneading, massing, sieving, stirring and the like. For example, a basic amine or a basic amino acid, or a cyclodextrin may be directly mixed with the active ingredient (addition in a powder state), or a solvent is added to the mixture, followed by conventional kneading, granulating and drying. Alternatively, a basic amine or a basic amino acid, or a cyclodextrin is dissolved in a suitable solvent, then the solution is uniformly mixed with the active ingredient, followed by conventional kneading, granulating and drying (addition in a liquid state). In the case of addition in a liquid state, any solvent which does not exert undesirable influence on the active ingredient, for example, water, dimethylformamide, acetone, ethanol, propyl alcohol, isopropyl alcohol, butyl alcohol, methylene chloride, trichloroethane etc., can be employed. After completion of blending, the material is subjected to a conventional molding process under pressurization to prepare tablets containing the active ingredient. The molding under pressurization means that a material is compressed under pressurization into a desired form, which most generally refers to tableting.

It is also possible to add a variety of carriers to be employed for preparation making to the solid pharmaceutical composition (e.g. solid preparations) of the present invention in an adequate step. Examples include, but not limited to, fillers, diluents, disintegrants, glidants, excipients, binders, lubricants, colorant, flavoring agents, odor-improving agents, wetting agents, and the like.

Suitable fillers and diluents include, but are not limited to, cellulose-derived materials like powdered cellulose, microcrystalline cellulose (e.g. Avicel®), microfine cellulose, methyl cellulose, ethyl cellulose, hydroxyethyl cellulose, hydroxypropylcellulose, hydroxypropylmethylcellulose, carboxymethylcellulose salts and other substituted and unsubstituted celluloses; starch; pregelatinized starch; lactose; talc; waxes; sugars; sugar alcohols like mannitol and sorbitol; acrylate polymers and copolymers; dextrates; dextrin; dextrose; maltodextrin; pectin; gelatin; inorganic diluents like calcium carbonate, dibasic calcium phosphate dihydrate, tribasic calcium phosphate, magnesium carbonate, magnesium oxide, sodium chloride and other diluents known to the pharmaceutical industry.

Suitable disintegrants include, but are not limited to, croscarmellose sodium (e.g. Ac Di Sol®, Primellose®), crospovidone (e.g. Kollidon®, Polyplasdone®), microcrystalline cellulose, polacrilin potassium, powdered cellulose, pregelatinized starch, sodium starch glycolate (e.g. Explotab®, Primoljel®) and starch, and the like.

Glidants can be added to improve the flowability of a solid composition before compaction and to improve the accuracy of dosing especially during compaction and capsule filling. Excipients that may function as glidants include, but are not limited to, colloidal silicon dioxide, magnesium trisilicate, powdered cellulose, talc, and the like.

Suitable excipients that may be incorporated into the formulation include, but are not limited to, microcrystalline cellulose (for example, Avicel PH101, PH101 (manufactured by Asahi Kasei Corporation)), carboxymethylcellulose calcium, corn starch, wheat starch, lactose, sucrose, glucose, calcium sulfate, calcium phosphate, sodium chloride, and so on. In addition, such excipients include preservatives, surfactants, antioxidants, or any other excipient commonly used in the pharmaceutical industry.

Suitable binders that may be incorporated into the formulation include, but are not limited to, water, ethanol, propanol, simple syrup, glucose solutions, starch solutions, gelatin solutions, gum arabic, gelatin, sodium alginate, methyl cellulose, carboxymethylcellulose, shellac, polyvinylpyrrolidone, crospovidone, hydroxypropylcellulose (which may be hereinafter referred to as HPC), hydroxypropylmethylcellulose, and the like. In addition, such binders include other binders used in wet or dry granulation and in direct compression tableting processes.

Suitable lubricants that may be incorporated into the formulation include, but are not limited to, magnesium stearate, talc, synthetic aluminum silicate, sodium lauryl sulfate, boric acid, magnesium oxide, paraffin, and the like. In addition, colorant, flavoring agents, odor-improving agents, wetting agents, and the like may be added.

Incidentally, in the case of using a crystalline compound whose specific gravity is relatively small as an active pharmaceutical ingredient, it is desirable to have the compound dispersed in advance in a thick liquid containing such a binder as HPC and water. Furthermore, the solid pharmaceutical composition of the present invention can be prepared into coated tablets as well.

The coating may be conducted by a method known per se. As the coating agents, conventional coating agents (e.g. hydroxypropylmethylcellulose, hydroxypropylcellulose, methylcellulose, polyvinylpyrrolidone etc.), and as auxiliary agents for coating, use is made of, for example, polyethylene glycol 6000, polysorbate (e.g. Tween 80 etc.), titanium oxide, and pigments such as red iron oxide can be used.

In the case of using the pharmaceutical composition of this invention for the treatment of diseases mediated by cyclooxygenase-2 in animals (e.g. man, dog, rabbit or rat), it can be administered orally as tablets, etc. The dosage ranges from 0.0075 to 15 mgA/kg per day, preferably from 0.07 to 7.2 mgA/kg per day in terms of the active pharmaceutical ingredient (wherein mgA means mg weight of the active pharmaceutical ingredient based on the free acid). The dosage can be increased or decreased depending on the disease or condition.

When the pharmaceutical composition is in the dosage form of a capsule, the capsule may contain the pharmaceutical composition of the invention in a form of uncompressed or compressed granulates or powder mixes, etc. The capsules may be covered with either a hard shell or a soft shell. The shells may be made from, but not limited to gelatin and optionally contain a plasticizer such as glycerin and sorbitol, and an opacifying agent or colorant.

Methods of administration of a pharmaceutical composition for treating diseases mediated by cyclooxygenase-2 in the present invention are not specifically restricted, and can be administered in various preparations depending on the age, sex, and symptoms of the patient. Suitable routes for administrating a pharmaceutical composition may include, but not limited to, oral, buccal, and rectal administration. Although the most suitable administration in any given case will depend on the nature and severity of the condition being treated, the most preferred route of administration of the present invention is oral. The dosages may be conveniently presented in unit dosage form and prepared by any of the methods commonly known in the pharmaceutical arts.

Having described the invention with reference to certain preferred embodiments, other embodiments will become apparent to one skilled in the art from consideration of the specification. The invention is further explained by reference to the following examples, but they are just examples, which never limit the present invention. It will be apparent to those skilled in the art that many modifications, both to materials and methods, may be practiced without departing from the scope of the invention.

EXAMPLES

The present invention is explained in more detail in the following by referring to Reference Examples and Examples, which are not to be construed as limitative but just typical examples.

Compound A can be prepared using any method known in the art (for example, patent literature 1, JP Patent No. P4577534).

Example 1

Compound A Tablet Containing Tromethamine which is a Basic Amine

Formulation

Compound A 60 mg tablet containing tromethamine is prepared according to the formulation described in Table 1, Table 2, and Table 3. Other dosage tablets are prepared in proportion to dosage depending on weight % of each ingredient. A tablet containing another basic amine such as triethanolamine, diethanolamine, monoethanolamine, and the like is prepared in a similar manner to the formulation in tromethamine. Actually, the tablet is prepared by replacing tromethamine in Table 1, Table 2, and Table 3 with another basic amine.

Manufacturing Process 1

Weigh each Compound A milled with a rasping 0.006 inch screen at 1800 rpm, tromethamine and mannitol which are both milled with a rasping 0.018 inch screen at 1800 rpm. Add microcrystalline cellulose PH102 into the PK-blender and blend for 1 minute to coat the surfaces. Add Compound A, milled tromethamine, sodium croscarmellose, and milled mannitol in this order. Blend for 10 minutes and then add magnesium stearate (lubricant) and blend for 2 minutes. Mill with a rasping 0.062 inch screen at 900 rpm and add milled granules and the extra granular magnesium stearate into a V-blender and blend for 2 minutes. Prepare Compound A 60 mg tablet containing tromethamine with a rotary automated tablet press.

TABLE 1

Formulation 1: Compound A tablet formulation containing tromethamine.

| Ingredient | Weight (%) | mg/tablet |
|---|---|---|
| Intra granule | | |
| Compound A | 30.0 | 60.0 |
| tromethamine | 30.0 | 60.0 |
| mannitol | 18.75 | 37.5 |
| microcrystalline cellulose PH102 | 18.0 | 36.0 |
| sodium croscarmellose | 2.0 | 4.0 |
| (intra granular) magnesium stearate | 0.25 | 0.5 |
| Extra granule | | |
| (extra granular) magnesium stearate | 1.0 | 2.0 |
| Total | 100.0 | 200.0 |

Manufacturing Process 2

Prepare the tablet in a similar manner to the manufacturing process 1. Actually, prepare Compound A 60 mg tablet using ingredients described in Table 2.

TABLE 2

Formulation 2: Compound A tablet formulation containing tromethamine.

| Ingredient | Weight (%) | mg/tablet |
|---|---|---|
| Compound A | 30.0 | 60.0 |
| tromethamine | 30.0 | 60.0 |
| lactose | 17.0 | 34.0 |
| microcrystalline cellulose PH102 | 17.0 | 34.0 |
| sodium croscarmellose | 5.0 | 10.0 |
| silicon dioxide | 0.5 | 1.0 |
| magnesium stearate | 0.5 | 1.0 |
| Total | 100.0 | 200.0 |

Manufacturing Process 3

Weigh each Compound A milled with a rasping 0.006 inch screen at 1800 rpm, tromethamine, mannitol, microcrystalline cellulose, sodium croscarmellose, and povidone which are all milled with a rasping 0.039 inch screen at 1800 rpm.

Transfer Compound A, tromethamine, mannitol, microcrystalline cellulose, sodium croscarmellose, and povidone into a granulator, and blend homogeneously for 1 minute.

Stir the mixture, and granulate during adding purified water. Dry the granule with drying machine at 50 to 55° C. Subject the dried granule to particle size regulation with a rasping 0.039 inch screen. Weigh sodium croscarmellose, and magnesium stearate both milled with a rasping 0.010 inch screen. Add dried granules and sodium croscarmellose to a blender and blend at 49 rpm for 10 minutes. Add magnesium stearate and stir the mixture at the same rpm for additional 2 minutes. Prepare Compound A 60 mg tablet containing tromethamine with a single punch tableting.

TABLE 3

Formulation 3: Compound A tablet formulation containing tromethamine.

| Ingredient | Weight (%) | mg/tablet |
|---|---|---|
| Compound A | 30.0 | 60.0 |
| tromethamine | 30.0 | 60.0 |
| mannitol | 17.0 | 34.0 |
| microcrystalline cellulose PH101 | 15.0 | 30.0 |
| sodium croscarmellose | 5.0 | 10.0 |
| povidone | 2.0 | 4.0 |
| magnesium stearate | 1.0 | 2.0 |
| Total | 100.0 | 200.0 |

Example 2

Compound A Capsule Containing Tromethamine which is a Basic Amine

Formulation

Compound A 60 mg capsule containing tromethamine is prepared according to the formulation described in Table 4. Other dosage capsules are prepared in proportion to dosage depending on weight % of each ingredient. A capsule containing another basic amine such as triethanolamine, diethanolamine, monoethanolamine, and the like is prepared in a similar manner to the formulation in tromethamine. Actually, the capsule is prepared by replacing tromethamine in Table 4 with another basic amine.

Manufacturing Process

Blend Compound A, tromethamine, lactose monohydrate, microcrystalline cellulose PH102, hypromellose, and sodium croscarmellose, which are all milled with a rasping #120 mesh screen, in a high-shear wet granulator.

Add a solution of polysorbate 80 in purified water into the granulator. Mill the granulated material with a rasping 0.25 inch screen, followed by drying on the tray. Mill the granulated material with a rasping 0.039 inch screen. Add magnesium stearate to the milled granules and blend them in a V-blender. Pack the powder mixture into capsules.

TABLE 4

Formulation: Compound A capsule formulation containing tromethamine.

| Ingredient | Weight (%) | mg/capsule |
|---|---|---|
| Compound A | 30.0 | 60.0 |
| tromethamine | 30.0 | 60.0 |
| lactose monohydrate | 32.0 | 64.0 |
| microcrystalline cellulose PH102 | 2.5 | 5.0 |
| hypromellose | 2.5 | 5.0 |
| sodium croscarmellose | 2.5 | 5.0 |
| polysorbate 80 | 0.25 | 0.5 |
| magnesium stearate | 0.25 | 0.5 |
| Total | 100.0 | 200.0 |

Example 3

Compound A Tablet Containing Meglumine which is a Basic Amine

Formulation

Prepare the tablet using meglumine instead of tromethamine described in Table 3.

Manufacturing Process

Prepare the tablet in a similar manner to the manufacturing process 3 in example 1. Actually, prepare the Compound A 60 mg tablet containing meglumine using meglumine instead of tromethamine described in Table 3.

Example 4

Compound A Tablet Containing Lysine which is a Basic Amino Acid

Formulation

Compound A 60 mg tablet containing lysine is prepared according to the formulation described in Table 5 and Table 6. Other dosage tablets are prepared in proportion to dosage depending on weight % of each ingredient. A tablet containing another amino acid such as arginine, histidine, tryptophan, ornithine, and the like is prepared in a similar manner to the formulation in lysine. Actually, the tablet is prepared by replacing lysine in Table 5 and Table 6 with another amino acid.

Manufacturing Process

Prepare the tablet in a similar manner to the manufacturing process 2 in example 1. Actually, prepare the Compound A 60 mg tablet containing lysine using ingredients described in Table 5.

TABLE 5

Formulation 1: Compound A tablet formulation containing lysine.

| Ingredient | Weight (%) | mg/tablet |
|---|---|---|
| Compound A | 30.0 | 60.0 |
| lysine | 30.0 | 60.0 |
| lactose | 17.0 | 34.0 |
| microcrystalline cellulose PH102 | 17.0 | 34.0 |
| sodium croscarmellose | 5.0 | 10.0 |
| silicon dioxide | 0.5 | 1.0 |
| magnesium stearate | 0.5 | 1.0 |
| Total | 100.0 | 200.0 |

Manufacturing Process 2

Prepare the tablet in a similar manner to the manufacturing process 3 in example 1. Actually, prepare the Compound A 60 mg tablet containing lysine using lysine instead of tromethamine described in the manufacturing process 3.

TABLE 6

Formulation 2: Compound A tablet formulation containing lysine.

| Ingredient | Weight (%) | mg/tablet |
|---|---|---|
| Compound A | 30.0 | 60.0 |
| lysine | 30.0 | 60.0 |
| mannitol | 17.0 | 34.0 |
| microcrystalline cellulose PH101 | 15.0 | 30.0 |
| sodium croscarmellose | 5.0 | 10.0 |
| povidone | 2.0 | 4.0 |
| magnesium stearate | 1.0 | 2.0 |
| Total | 100.0 | 200.0 |

Example 5

Compound A Tablet Containing Arginine which is a Basic Amino Acid

Formulation

Prepare the tablet using arginine instead of lysine described in Table 6.

Manufacturing Process

Prepare the tablet in a similar manner to the manufacturing process 3 in example 1. Actually, prepare the Compound A 60 mg tablet containing arginine using arginine instead of tromethamine described in the manufacturing process 3.

Example 6

Compound A Tablet Containing Hydroxypropyl-β-Cyclodextrin which is a Clathrate Compound Formulation Compound A 60 mg tablet containing a clathrate compound is prepared according to the formulation described in Table 7 and Table 8. Other dosage tablets are prepared in proportion to dosage depending on weight % of each ingredient. A tablet containing another clathrate compound such as β-cyclodextrin, sodium sulfobutylether-β-cyclodextrin (SBECD), and the like is prepared in a similar manner to the formulation in hydroxypropyl-β-cyclodextrin. Actually, the tablet is prepared by replacing hydroxypropyl-β-cyclodextrin in Table 7 and Table 8 with another clathrate compound.

Manufacturing Process 1

Weigh Compound A and each ingredient which are all milled with a rasping 0.006 inch screen at 1800 rpm. Add microcrystalline cellulose PH102 into a V-blender and blend for 1 minute. Add Compound A, hydroxypropyl-β-cyclodextrin, sodium croscarmellose, and lactose in this order. Blend for 10 minutes. Add magnesium stearate milled with a rasping #20 mesh screen into the V-blender and blend for 2 minutes. Prepare Compound A 60 mg tablet containing hydroxypropyl-β-cyclodextrin with a rotary automated tablet press.

TABLE 7

Formulation 1: Compound A tablet formulation containing hydroxypropyl-β-cyclodextrin.

| Ingredient | Weight (%) | mg/tablet |
|---|---|---|
| Compound A | 30.0 | 60.0 |
| hydroxypropyl-β-cyclodextrin | 30.0 | 60.0 |
| lactose monohydrate | 18.2 | 36.5 |
| microcrystalline cellulose PH102 | 18.2 | 36.5 |
| sodium croscarmellose | 2.5 | 5.0 |
| magnesium stearate | 1.0 | 2.0 |
| Total | 100.0 | 200.0 |

Manufacturing Process 2

Prepare the tablet in a similar manner to the manufacturing process 3 in example 1. Actually, prepare the Compound A 60 mg tablet containing hydroxypropyl-β-cyclodextrin using hydroxypropyl-β-cyclodextrin instead of tromethamine described in the manufacturing process 3.

TABLE 8

Formulation 2: Compound A tablet formulation containing hydroxypropyl-β-cyclodextrin.

| Ingredient | Weight (%) | mg/tablet |
|---|---|---|
| Compound A | 30.0 | 60.0 |
| hydroxypropyl-β-cyclodextrin | 30.0 | 60.0 |
| mannitol | 17.0 | 34.0 |
| microcrystalline cellulose PH101 | 15.0 | 30.0 |
| sodium croscarmellose | 5.0 | 10.0 |
| povidone | 2.0 | 4.0 |
| magnesium stearate | 1.0 | 2.0 |
| Total | 100.0 | 200.0 |

Comparative Example 1

Compound A Solution Formulation

Formulation

Compound A 360 mg/60 ml solution (OPC, Oral Powder Constitution: a solution simply dissolved the active ingredient) was prepared by the formulation described in Table 9. Other concentration solutions are prepared in a similar manner.

Manufacturing Process

Measure 20 mL of tromethamine using sylinge with needle and add it to the OPC vial containing 360 mg of compound A. Dissolve Compound A by shaking the vial. Measure 10 mL of sterile water using sylinge with needle and put it into the OPC vial. Shake well. Open the lid, put it in 120 mL brown bottles for administration. Further wash OPC vial with 30 mL sterile water, and put the washed liquid into the brown bottle for administration.

TABLE 9

Formulation: Compound A soluion (OPC) formulation.

| Material | Quantity |
|---|---|
| Compound A | 360 mg |
| tromethamine | 20 mL |
| sterile water | 40 mL |

Comparative Example 2

Compound A Standard Tablet Formulation
(Conventional Tablet Formulations which do not Contain Basic Amines, Basic Amino Acids, Cyclodextrins)

Formulation

The standard tablet is prepared by the formulation described in Table 10 and Table 11. Other dosage tablets are prepared in proportion to dosage depending on weight % of each ingredient.

Manufacturing Process 1

Weigh Compound A and ingredients which are all milled with a rasping 0.018 inch screen at 1800 rpm. Add microcrystalline cellulose PH102 into a V-blender and blend for 1 minute. Add Compound A, sodium croscarmellose, silicon dioxide, and lactose monohydrate in this order. Blend for 10 minutes. Add magnesium stearate milled with a rasping #20 mesh screen into the V-blender and blend for 2 minutes. Prepare Compound A 60 mg standard tablet with a rotary automated tablet press.

TABLE 10

Formulation 1: Compound A standard tablet formulation.

| Ingredient | Weight (%) | mg/tablet |
|---|---|---|
| Compound A | 30.0 | 60.0 |
| lactose monohydrate | 45.0 | 90.0 |
| microcrystalline cellulose PH102 | 22.0 | 44.0 |
| sodium croscarmellose | 2.0 | 4.0 |
| silicon dioxide | 0.5 | 1.0 |
| magnesium stearate | 0.5 | 1.0 |
| Total | 100.0 | 200.0 |

Manufacturing Process 2

Weigh each Compound A milled with a rasping 0.006 inch screen at 1800 rpm, lactose, microcrystalline cellulose, and sodium croscarmellose which are all milled with a rasping 0.039 inch screen. Transfer Compound A, lactose, microcrystalline cellulose, and sodium croscarmellose into a blender, and blend the mixture at 49 rpm for 5 minutes. Weigh magnesium stearate milled with a rasping 0.010 inch screen and add it to the mixture above, and then blend the mixture at 49 rpm for 2 minutes. Prepare Compound A 60 mg standard tablet with a single punch tableting.

TABLE 11

Formulation 2: Compound A standard tablet formulation.

| Ingredient | Weight (%) | mg/tablet |
|---|---|---|
| Compound A | 30.0 | 60.0 |
| mannitol | 45.5 | 91.0 |
| microcrystalline cellulose PH101 | 22.0 | 44.0 |
| sodium croscarmellose | 2.0 | 4.0 |
| magnesium stearate | 0.5 | 1.0 |
| Total | 100.0 | 200.0 |

Comparative Example 3

Compound A Tablet Formulation Containing a Basic Alkaline-Earth Metal Salt

Formulation

Compound A 60 mg tablet containing calcium hydroxide which is a basic alkaline-earth metal salt is prepared according to the formulation described in Table 12 and Table 13. Other dosage tablets are prepared in proportion to dosage depending on weight % of each ingredient. A tablet containing another basic alkaline-earth metal salt such as calcium carbonate, and the like is prepared in a similar manner to the formulation in calcium hydroxide. Actually, the tablet is prepared by replacing calcium hydroxide in Table 12 and Table 13 with another basic alkaline-earth metal salt.

Manufacturing Process 1

Prepare the tablet using ingredients described in Table 12 in a similar manner to the manufacturing process 2 in example 1. Actually, prepare the Compound A 60 mg tablet containing calcium hydroxide using ingredients described in Table 12.

TABLE 12

Formulation 1: Compound A tablet formulation containing a basic inorganic salt.

| Ingredient | Weight (%) | mg/tablet |
|---|---|---|
| Compound A | 30.0 | 60.0 |
| calcium hydroxide | 30.0 | 60.0 |
| lactose | 17.0 | 34.0 |
| microcrystalline cellulose PH102 | 17.0 | 34.0 |
| sodium croscarmellose | 5.0 | 10.0 |
| silicon dioxide | 0.5 | 1.0 |
| magnesium stearate | 0.5 | 1.0 |
| Total | 100.0 | 200.0 |

Manufacturing Process 2

Prepare the tablet in a similar manner to the manufacturing process 3 in example 1. Actually, prepare the Compound A 60 mg tablet containing calcium hydroxide using calcium hydroxide instead of tromethamine described in the manufacturing process 3.

TABLE 13

Formulation 2: Compound A tablet formulation containing calcium hydroxide.

| Ingredient | Weight (%) | mg/tablet |
|---|---|---|
| Compound A | 30.0 | 60.0 |
| calcium hydroxide | 30.0 | 60.0 |
| mannitol | 17.0 | 34.0 |
| microcrystalline cellulose PH101 | 15.0 | 30.0 |
| sodium croscarmellose | 5.0 | 10.0 |
| povidone | 2.0 | 4.0 |
| magnesium stearate | 1.0 | 2.0 |
| Total | 100.0 | 200.0 |

Comparative Example 4

Compound a Tablet Formulation Containing Calcium Carbonate which is a Basic Alkaline-Earth Metal Salt Formulation Prepare the tablet using calcium carbonate instead of calcium hydroxide described in Table 13.

Manufacturing Process

Prepare the tablet in a similar manner to the manufacturing process 3 in example 1. Actually, prepare the Compound A 60 mg tablet containing calcium carbonate using calcium carbonate instead of tromethamine described in the manufacturing process 3.

Comparative Example 5

Compound A Tablet Containing Magnesium Oxide which is a Basic Alkaline-Earth Metal Salt Formulation Compound A tablet containing magnesium oxide which is a basic alkaline-earth metal salt is prepared according to the formulation described in Table 14. Other dosage tablets are prepared in proportion to dosage depending on weight % of each ingredient. A tablet containing another basic alkaline-earth metal salt such as calcium carbonate, and the like is prepared in a similar manner to the formulation in calcium hydroxide. Actually, the tablet is prepared by replacing calcium hydroxide in Table 13 with another basic alkaline-earth metal salt.

Manufacturing Process

Prepare the tablet in a similar manner to the manufacturing process in comparative example 4. Actually, prepare the Compound A 60 mg tablet containing magnesium oxide using magnesium oxide instead of calcium hydroxide.

TABLE 14

Formulation: Compound A tablet formulation containing magnesium oxide.

| Ingredient | Weight (%) | mg/tablet |
|---|---|---|
| Compound A | 30.0 | 60.0 |
| magnesium oxide | 30.0 | 60.0 |
| mannitol | 17.0 | 34.0 |
| microcrystalline cellulose PH101 | 15.0 | 30.0 |
| sodium croscarmellose | 5.0 | 10.0 |
| povidone | 2.0 | 4.0 |
| magnesium stearate | 1.0 | 2.0 |
| Total | 100.0 | 200.0 |

Comparative Example 6

Compound A Capsule

Formulation

Compound A 1 mg capsule and 10 mg capsule were prepared according to the formulation described in Table 15. Other dosage capsules are prepared by adjusting the weight % of lactose monohydrate in proportion to weight of Compound A.

Manufacturing Process

Blend Compound A, lactose monohydrate, microcrystalline cellulose PH102, hypromellose, and sodium croscarmellose, which are all milled with a rasping #120 mesh screen, in a high-shear wet granulator. Add a solution of polysorbate 80 in purified water into the said granulator. Mill the granulated material with a rasping 0.25 inch screen, followed by drying on the tray. Mill the granulated material with a rasping 0.039 inch screen. Add magnesium stearate to the milled granules and blend them in a V-blender. Pack the powder mixture into capsules.

TABLE 15

Formulation: Compound A capsule formulation.

| Ingredient | 1 mg capsule weight (mg) | 10 mg capsule weight (mg) |
|---|---|---|
| Compound A | 1.0 | 10.0 |
| lactose monohydrate | 83.0 | 74.0 |
| microcrystalline cellulose PH102 | 5.0 | 5.0 |
| hypromellose | 5.0 | 5.0 |
| sodium croscarmellose type SD-711 | 5.0 | 5.0 |
| polysorbate 80 | 0.5 | 0.5 |
| purified water | Note) | Note) |
| magnesium stearate | 0.5 | 0.5 |
| Total | 100.0 | 100.0 |

Hard-gelatin capsule which is white-semitransparent and #3 size. Note) Purified water is used in the granulation process and is removed in the drying process.

[Dissolution Test]

The formulations prepared above are subject to the dissolution test, paddle method. HPLC method is used as a measurement method.

Results

FIG. 1 shows each dissolution rate (%) amount over time in a Compound A tablet containing tromethamine and a standard tablet. It can be seen that the dissolution rate of Compound A tablet containing tromethamine is higher than that of the standard formulation preparation.

Figure 2:
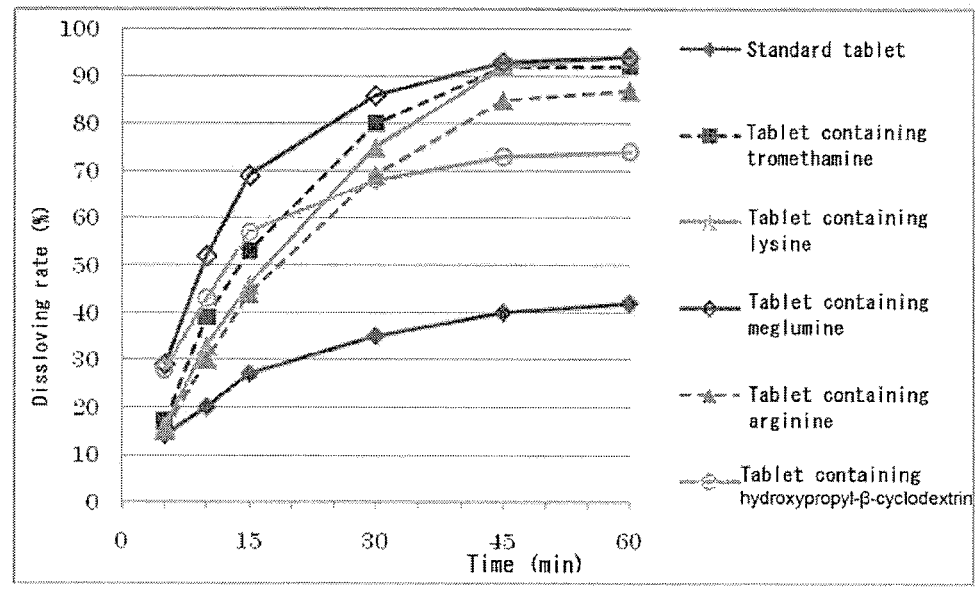
FIG. 2 A graph showing each dissolution amount over time in a tablet of Compound A containing tromethamine which is prepared by the manufacturing process 3 in example 1; a tablet of Compound A containing meglumine which is prepared by example 3; a tablet of Compound A containing lysine which is prepared by the manufacturing process 2 in example 4; a tablet of Compound A containing arginine which is prepared by example 5; a tablet of Compound A containing β-cyclodextrin which is prepared by the manufacturing process 2 in example 6; and a standard tablet, which is prepared by the manufacturing process 2 in comparative example 2.

FIG. 2 shows each dissolution rate (%) amount over time in a Compound A tablet containing meglumine, lysine, arginine, or hydroxypropyl-β-cyclodextrin and, and a standard tablet. It can be seen that the dissolution rate of each tablet is higher than that of the standard formulation preparation.

Thus, Compound A tablets containing a basic amine or a basic amino acid, or a cyclodextrin show a good dissolution rate compared with the standard tablet formulation.

Figure 3:
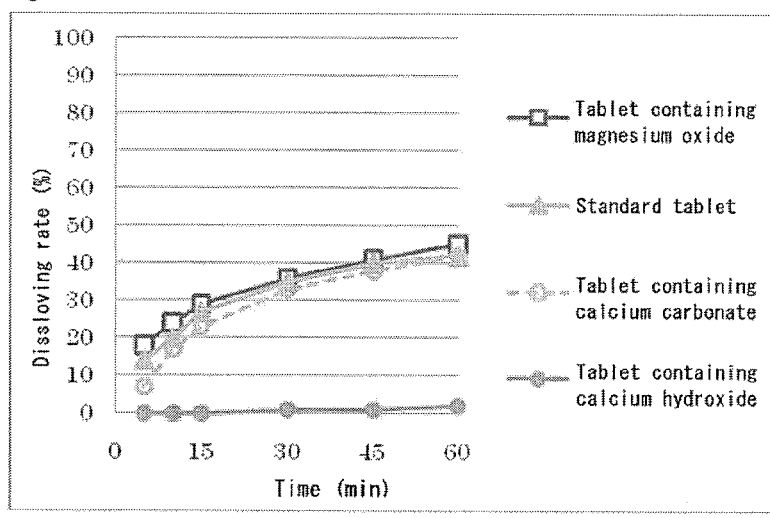
FIG. 3 A graph showing each dissolution amount over time in a tablet of Compound A containing calcium hydroxide which is prepared by the manufacturing process 2 in comparative example 3; calcium carbonate which is prepared by comparative example 4; magnesium oxide which is prepared by comparative example 5; and a standard tablet which is prepared by the manufacturing process 2 in comparative example 2.

On the contrary, as shown in FIG. 3, dissolution rate of Compound A tablets containing calcium hydroxide, calcium carbonate, magnesium oxide is less than 50% even at the time of 60 minutes, which is poor dissolution comparing with that of the tablets of the present invention.

[Stability Test]

The formulations prepared above are subject to the stability test for storage. HPLC method is used as a measurement method.

Results

As a result of the stability test, tablets of the present invention show good stability.

[Pharmacokinetic Study]

Administer pharmaceutical compositions prepared above to human, collect their blood, and measure the blood concentration. Blood concentrations of Compound A are measured with HPLC-MS.

Results

Figure 4:
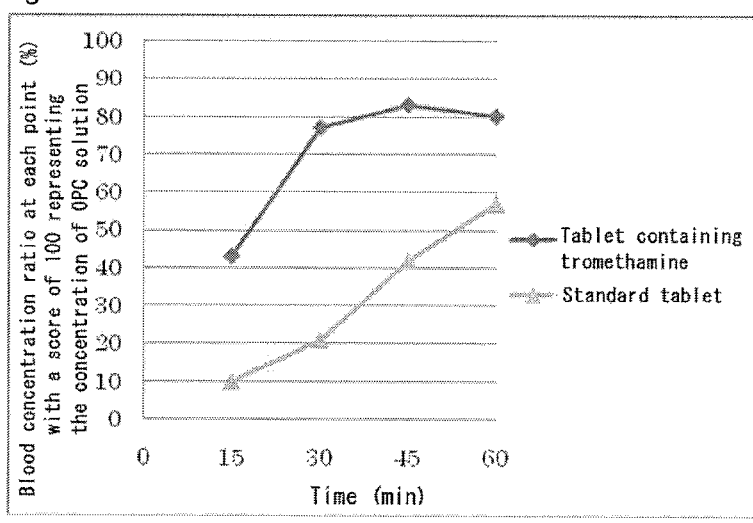
FIG. 4 A graph showing the ratio (%) of blood concentration over time in a Compound A tablet containing tromethamine which is prepared by the manufacturing process 3 in example 1, and in a Compound A standard tablet which is prepared by comparative example 2; wherein each blood concentration is divided by the blood concentration at corresponding time in a Compound A OPC solution prepared by comparative example 1.
Figure 5:
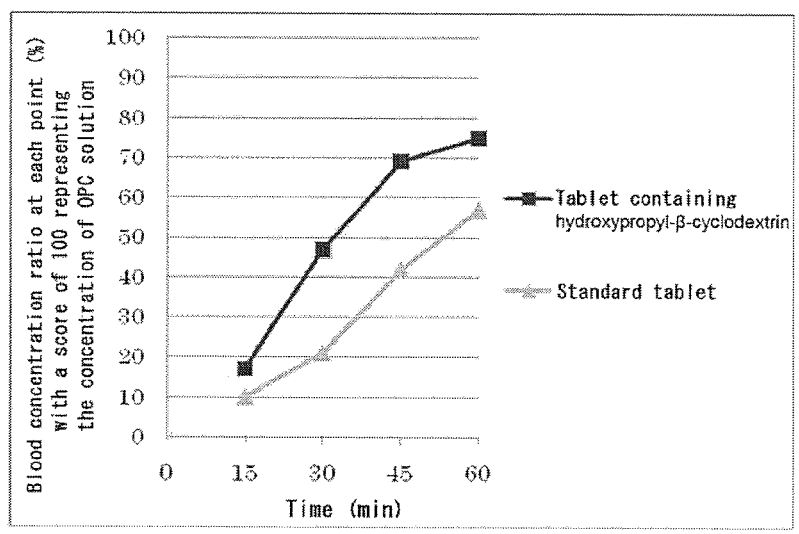
FIG. 5 A graph showing the ratio (%) of blood concentration over time in a Compound A tablet containing hydroxypropyl-β-cyclodextrin which is prepared by the manufacturing process 1 in example 6, and in a Compound A standard tablet which is prepared by comparative example 2; wherein each blood concentration is divided by the blood concentration at corresponding time in a Compound A OPC solution prepared by comparative example 1.

FIG. 4 and FIG. 5 show the ratio (%) of blood concentration over time in a Compound A tablet containing tromethamine which is prepared by the manufacturing process 2 in example 1, and in a Compound A tablet containing β-cyclodextrin which is prepared by the manufacturing process 1 in example 6, respectively, and together with in a Compound A standard tablet which is prepared by comparative example 2; wherein each blood concentration is divided by the blood concentration at corresponding time in a Compound A OPC solution prepared by comparative example 1.

It can be seen that in FIG. 4 the blood concentration of the tablet containing tromethamine reach four times as high as that of the standard tablet at 15 minutes post dose, and reach as high as that of OPC solution. Further, as shown in Table 16, the blood concentration in case of administering the tablet containing tromethamine is higher than that in case of administering capsule, and the AUC in tablet containing tromethamine is also three times as high as that in capsule.

FIG. 5 and Table 16 show the results in the case of using the tablet containing hydroxypropyl-β-cyclodextrin.

It can be seen that in FIG. 5 the blood concentration in the case of administering the standard tablet is just 10 to 20% comparing with that in the case of OPC solution at 15 minutes and 30 minutes post dose, but on the contrary, the blood concentration in the case of administering the tablet containing cyclodextrin is twice as high as that in the case of the standard tablet at 15 minutes and 30 minutes post dose, and in addition it is as high as that in the case of OPC solution at 1 hour post dose. Furthermore, as shown in Table 16, the blood concentration in the case of administering the tablet containing hydroxypropyl-β-cyclodextrin is higher than that in the case of administering the capsule, and the area under the blood concentration curve (AUC) is also doubled.

TABLE 16

Comparison of area under the blood concentration curve (AUC) among the Compound A OPC solution prepared by comparative example 1, the capsule agent prepared by comparative example 6, and Compound A tablet containing tromethamine prepared by the manufacturing process 1 in example 1.

| | AUC (0-2 hr)/dose (μg*hr/ml) |
|---|---|
| Compound A OPC solution | 0.13 |
| Tablet containing hydroxypropyl-β-cyclodextrin | 0.07 |
| Tablet containing tromethamine | 0.11 |
| Capsule | 0.038 |

Similarly, good results are obtained in the case of using tablets containing a basic amino acid such as lysine, arginine, histidine, tryptophan, ornithine, and the like, which is disclosed in the present invention.

However, when a tablet containing a basic inorganic salt such as calcium hydroxide, calcium carbonate, and the like is used, only less effect on improving the absorption is observed as compared with the tablets of the present invention.

As mentioned in the present examples and comparative examples, it is concluded that the tablet which is a pharmaceutical composition of the present inventions comprising adding a basic amine or basic amino acid, or a cyclodextrin to Compound A of the third generation coxib-compound can prevent from decreasing the blood concentration, AUC and bioavailability.

INDUSTRIAL APPLICABILITY

The present invention provide a pharmaceutical composition which can prevent from decreasing the blood concentration, AUC, and bioavailability; wherein the pharmaceutical composition has a coxib-compound with cyclooxygenase-2 inhibitory activity as an active pharmaceutical ingredient and incorporated a basic amine, a basic amino acid or a cyclodextrin. The pharmaceutical composition has also good stability, which is useful for drugs.

The invention claimed is:

1. A pharmaceutical composition comprising a third-generation coxib-compound or a pharmaceutically acceptable salt thereof, wherein the pharmaceutical composition contains at least one excipient selected from a basic amine, a basic amino acid, and a cyclodextrin in the range of 0.5% (weight/whole pharmaceutical composition weight) or more.

2. The pharmaceutical composition according to claim 1, wherein at least one excipient selected from a basic amine, a basic amino acid, and a cyclodextrin is contained in the range of 5 to 70% (weight/whole pharmaceutical composition weight).

3. The pharmaceutical composition according to claim 1, wherein the third-generation coxib-compound is a compound represented by the formula (I):

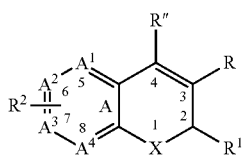

(I)

wherein X is selected from O, S and NR$^a$;
wherein R$^a$ is selected from hydrido, $C_1$-$C_3$-alkyl, (optionally substituted phenyl)-methyl, and phenylmethyl; wherein the phenyl ring is substituted by 1 to 3 substituents independently selected from $C_1$-$C_6$-alkyl, hydroxyl, halo, $C_1$-$C_6$-haloalkyl, nitro, cyano, $C_1$-$C_6$-alkoxy and $C_1$-$C_6$-alkylamino;
wherein R is carboxyl;
wherein R″ is selected from hydrido and $C_2$-$C_6$-alkenyl;
wherein R$^1$ is selected from $C_1$-$C_3$-perfluoroalkyl, chloro, $C_1$-$C_6$-alkylthio, nitro, cyano and cyano-$C_1$-$C_3$-alkyl;
wherein R$^2$ is one or more radicals independently selected from hydrido; halo; $C_1$-$C_6$-alkyl; $C_2$-$C_6$-alkenyl; $C_2$-$C_6$-alkynyl; halo-$C_2$-$C_6$-alkynyl; phenyl-$C_1$-$C_6$-alkyl; phenyl-$C_2$-$C_6$-alkynyl; phenyl-$C_2$-$C_6$-alkenyl; $C_1$-$C_3$-alkoxy; methylenedioxy; $C_1$-$C_3$-alkoxy-$C_1$-$C_3$-alkyl; $C_1$-$C_3$-alkylthio; $C_1$-$C_3$-alkylsulfinyl; phenyloxy; phenylthio; phenylsulfinyl; $C_1$-$C_3$-haloalkyl-$C_1$-$C_3$-hydroxyalkyl; phenyl-$C_1$-$C_3$-alkoxy-$C_1$-$C_3$-alkyl; $C_1$-$C_3$-haloalkyl; $C_1$-$C_3$-haloalkoxy; $C_1$-$C_3$-haloalkylthio; $C_1$-$C_3$-hydroxyalkyl; hydroxyimino-$C_1$-$C_3$-alkyl; $C_1$-$C_6$-alkylamino; nitro; cyano; amino; amino sulfonyl; N-($C_1$-$C_6$-alkyl)aminosulfonyl; N-arylaminosulfonyl; N-heteroarylaminosulfonyl; N-(phenyl-$C_1$-$C_6$-alkyl)aminosulfonyl; N-(heteroaryl-$C_1$-$C_6$-alkyl)aminosulfonyl; phenyl-$C_1$-$C_3$-alkylsulfonyl; 5- to 8-membered heterocyclylsulfonyl; $C_1$-$C_6$-alkylsulfonyl; phenyl; optionally substituted phenyl substituted by one or more radicals selected from chloro, fluoro, bromo, methoxy, methylthio and methylthiosulfonyl; 5- to 9-membered heteroaryl; chloro substituted thienyl; phenyl-$C_1$-$C_6$-alkylcarbonyl; phenylcarbonyl; 4-chlorophenylcarbonyl; 4-hydroxyphenylcarbonyl; 4-trifluoromethylphenylcarbonyl; 4-methoxyphenylcarbonyl; aminocarbonyl; formyl; and $C_1$-$C_6$-alkylcarbonyl;
wherein the A ring atoms A$^1$, A$^2$, A$^3$ are carbon and A$^4$ is carbon or nitrogen, or wherein R$^2$ together with ring A forms a naphthyl, benzofurylphenyl, or quinolyl radical;
or an isomer thereof.

4. The pharmaceutical composition according to claim 1, wherein the third-generation coxib-compound is selected from the group consisting of 6-chloro-2-trifluoromethyl-2H-1-benzopyran-3-carboxylic acid;
6-chloro-7-methyl-2-trifluoromethyl-2H-1-benzopyran-3-carboxylic acid;
8-(1-methylethyl)-2-trifluoromethyl-2H-1-benzopyran-3-carboxylic acid;
6-chloro-7-(1,1-dimethylethyl)-2-trifluoromethyl-2H-1-benzopyran-3-carboxylic acid;
6-chloro-8-(1-methylethyl)-2-trifluoromethyl-2H-1-benzopyran-3-carboxylic acid;
2-trifluoromethyl-3H-naphthopyran-3-carboxylic acid;
7-(1,1-dimethylethyl)-2-trifluoromethyl-2H-1-benzopyran-3-carboxylic acid;
6-bromo-2-trifluoromethyl-2H-1-benzopyran-3-carboxylic acid;
8-chloro-2-trifluoromethyl-2H-1-benzopyran-3-carboxylic acid;
6-trifluoromethoxy-2-trifluoromethyl-2H-1-benzopyran-3-carboxylic acid;
5,7-dichloro-2-trifluoromethyl-2H-1-benzopyran-3-carboxylic acid;
8-phenyl-2-trifluoromethyl-2H-1-benzopyran-3-carboxylic acid;
7,8-dimethyl-2-trifluoromethyl-2H-1-benzopyran-3-carboxylic acid;
6,8-bis(dimethylethyl)-2-trifluoromethyl-2H-1-benzopyran-3-carboxylic acid;
7-(1-methylethyl)-2-trifluoromethyl-2H-1-benzopyran-3-carboxylic acid;
7-phenyl-2-trifluoromethyl-2H-1-benzopyran-3-carboxylic acid;
6-chloro-7-ethyl-2-trifluoromethyl-2H-1-benzopyran-3-carboxylic acid;
6-chloro-8-ethyl-2-trifluoromethyl-2H-1-benzopyran-3-carboxylic acid;
6-chloro-7-phenyl-2-trifluoromethyl-2H-1-benzopyran-3-carboxylic acid;
6,7-dichloro-2-trifluoromethyl-2H-1-benzopyran-3-carboxylic acid;
6,8-dichloro-2-trifluoromethyl-2H-1-benzopyran-3-carboxylic acid;
2-trifluoromethyl-3H-naphtho[2,1-b]pyran-3-carboxylic acid;
6-chloro-8-methyl-2-trifluoromethyl-2H-1-benzopyran-3-carboxylic acid;
8-chloro-6-methyl-2-trifluoromethyl-2H-1-benzopyran-3-carboxylic acid;
8-chloro-6-methoxy-2-trifluoromethyl-2H-1-benzopyran-3-carboxylic acid;
6-bromo-8-chloro-2-trifluoromethyl-2H-1-benzopyran-3-carboxylic acid;
8-bromo-6-fluoro-2-trifluoromethyl-2H-1-benzopyran-3-carboxylic acid;
8-bromo-6-methyl-2-trifluoromethyl-2H-1-benzopyran-3-carboxylic acid;
8-bromo-5-fluoro-2-trifluoromethyl-2H-1-benzopyran-3-carboxylic acid;
6-chloro-8-fluoro-2-trifluoromethyl-2H-1-benzopyran-3-carboxylic acid;
6-bromo-8-methoxy-2-trifluoromethyl-2H-1-benzopyran-3-carboxylic acid;
6-[[(phenylmethyl)amino]sulfonyl]-2-trifluoromethyl-2H-1-benzopyran-3-carboxylic acid;
6-[(dimethylamino)sulfonyl]-2-trifluoromethyl-2H-1-benzopyran-3-carboxylic acid;
6-[(methylamino)sulfonyl]-2-trifluoromethyl-2H-1-benzopyran-3-carboxylic acid;
6-[(4-morpholino)sulfonyl]-2-trifluoromethyl-2H-1-benzopyran-3-carboxylic acid;
6-[(1,1-dimethylethyl)aminosulfonyl]-2-trifluoromethyl-2H-1-benzopyran-3-carboxylic acid;
6-[(2-methylpropyl)aminosulfonyl]-2-trifluoromethyl-2H-1-benzopyran-3-carboxylic acid;
6-methylsulfonyl-2-trifluoromethyl-2H-1-benzopyran-3-carboxylic acid;
8-chloro-6-[[(phenylmethyl)amino]sulfonyl]-2-trifluoromethyl-2H-1-benzopyran-3-carboxylic acid;
6-phenylacetyl-2-trifluoromethyl-2H-1-benzopyran-3-carboxylic acid;

6,8-dibromo-2-trifluoromethyl-2H-1-benzopyran-3-carboxylic acid;
8-chloro-5,6-dimethyl-2-trifluoromethyl-2H-1-benzopyran-3-carboxylic acid;
6,8-dichloro-(S)-2-trifluoromethyl-2H-1-benzopyran-3-carboxylic acid;
6-benzylsulfonyl-2-trifluoromethyl-2H-1-benzopyran-3-carboxylic acid;
6-[[N-(2-furylmethy)amino]sulfonyl]-2-trifluoromethyl-2H-1-benzopyran-3-carboxylic acid;
6-[[N-(2-phenylethy)amino]sulfonyl]-2-trifluoromethyl-2H-1-benzopyran-3-carboxylic acid;
6-iodo-2-trifluoromethyl-2H-1-benzopyran-3-carboxylic acid;
7-(1,1-dimethylethyl)-2-pentafluoroethyl-2H-1-benzopyran-3-carboxylic acid; and
6-chloro-2-trifluoromethyl-2H-1-benzothiopyran-3-carboxylic acid;
or an isomer thereof.

5. The pharmaceutical composition according to claim 1, wherein the third-generation coxib-compound is selected from the group consisting of
6-nitro-2-trifluoromethyl-2H-1-benzopyran-3-carboxylic acid;
6-chloro-8-methyl-2-trifluoromethyl-2H-1-benzopyran-3-carboxylic acid;
(S)-6-chloro-7-(1,1-dimethylethyl)-2-trifluoromethyl-2H-1-benzopyran-3-carboxylic acid;
2-trifluoromethyl-2H-naphtho[2,3-b]pyran-3-carboxylic acid;
6-chloro-7-(4-nitrophenoxy)-2-trifluoromethyl-2H-1-benzopyran-3-carboxylic acid;
(S)-6,8-dichloro-2-trifluoromethyl-2H-1-benzopyran-3-carboxylic acid;
6-chloro-2-trifluoromethyl-4-phenyl-2H-1-benzopyran-3-carboxylic acid;
6-(4-hydroxybenzoyl)-2-trifluoromethyl-2H-1-benzopyran-3-carboxylic acid;
2-(trifluoromethyl)-6-[(trifluoromethyl)thio]-2H-1-benzothiopyran-3-carboxylic acid;
6,8-dichloro-2-trifluoromethyl-2H-1-benzothiopyran-3-carboxylic acid;
6-(1,1-dimethylethyl)-2-trifluoromethyl-2H-1-benzothiopyran-3-carboxylic acid;
6,7-difluoro-1,2-dihydro-2-trifluoromethyl-3-quinolinecarboxylic acid;
6-chloro-1,2-dihydro-1-methyl-2-trifluoromethyl-3-quinolinecarboxylic acid;
6-chloro-2-trifluoromethyl-1,2-dihydro[1,8]naphthyridin-3-carboxylic acid; and
(S)-6-chloro-1,2-dihydro-2-trifluoromethyl-3-quinolinecarboxylic acid;
or an isomer thereof.

6. The pharmaceutical composition according to claim 1, wherein the basic amine or the basic amino acid is tromethamine, triethanolamine, diethanolamine, monoethanolamine, glucosamine, galactosamine, fructosamine, meglumine, N-ethyl glucamine, lysine, arginine, histidine, tryptophan or ornithine; and
the cyclodextrin is β-cyclodextrin, hydroxypropyl-β-cyclodextrin, or sodium sulfobutylether-β-cyclodextrin (SBECD).

7. The pharmaceutical composition according to claim 1, wherein the basic amine or the basic amino acid is tromethamine, meglumine, lysine, or arginine; and
the cyclodextrin is β-cyclodextrin or hydroxypropyl-β-cyclodextrin.

8. A process for preparing a pharmaceutical composition, as defined in claim 1, wherein the process comprises a step for combining
a third-generation coxib-compound or an isomer thereof, or a pharmaceutically acceptable salt thereof; and
a basic amine or a basic amino acid, or a cyclodextrin.

9. The process for preparing a pharmaceutical composition, as defined in claim 1, wherein the process comprises combining
a third-generation coxib-compound or an isomer thereof, or a pharmaceutically acceptable salt thereof; and
a basic amine or a basic amino acid, or a cyclodextrin;
with at least one carrier;
and subjecting the combination to grinding or milling, or granulation.

10. The process according to claim 8, wherein the process further comprises compressing the pharmaceutical composition into a solid dosage form.

11. The pharmaceutical composition according to claim 2, wherein the third-generation coxib-compound is a compound represented by the formula (I):

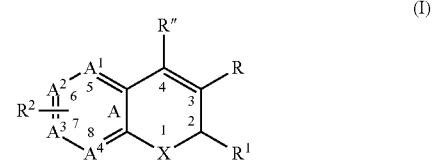

wherein X is selected from O, S and $NR^a$;
wherein $R^a$ is selected from hydrido, $C_1$-$C_3$-alkyl, (optionally substituted phenyl)-methyl, and phenylmethyl;
wherein the phenyl ring is substituted by 1 to 3 substituents independently selected from $C_1$-$C_6$-alkyl, hydroxyl, halo, $C_1$-$C_6$-haloalkyl, nitro, cyano, $C_1$-$C_6$-alkoxy and $C_1$-$C_6$-alkylamino;
wherein R is carboxyl;
wherein R" is selected from hydrido and $C_2$-$C_6$-alkenyl;
wherein $R^1$ is selected from $C_1$-$C_3$-perfluoroalkyl, chloro, $C_1$-$C_6$-alkylthio, nitro, cyano and cyano-$C_1$-$C_3$-alkyl;
wherein $R^2$ is one or more radicals independently selected from hydrido; halo; $C_1$-$C_6$-alkyl; $C_2$-$C_6$-alkenyl; $C_2$-$C_6$-alkynyl; halo-$C_2$-$C_6$-alkynyl; phenyl-$C_1$-$C_6$-alkyl; phenyl-$C_2$-$C_6$-alkynyl; phenyl-$C_2$-$C_6$-alkenyl; $C_1$-$C_3$-alkoxy; methylenedioxy; $C_1$-$C_3$-alkoxy-$C_1$-$C_3$-alkyl; $C_1$-$C_3$-alkylthio; $C_1$-$C_3$-alkyl sulfinyl; phenyloxy; phenylthio; phenylsulfinyl; $C_1$-$C_3$-haloalkyl-$C_1$-$C_3$-hydroxyalkyl; phenyl-$C_1$-$C_3$-alkoxy-$C_1$-$C_3$-alkyl; $C_1$-$C_3$-haloalkyl; $C_1$-$C_3$-haloalkoxy; $C_1$-$C_3$-haloalkylthio; $C_1$-$C_3$-hydroxyalkyl; hydroxyimino -$C_1$-$C_3$-alkyl; $C_1$-$C_6$-alkylamino; nitro; cyano; amino; aminosulfonyl; N-($C_1$-$C_6$-alkyl)aminosulfonyl; N-arylaminosulfonyl; N-heteroarylaminosulfonyl; N-(phenyl-$C_1$-$C_6$-alkyl)aminosulfonyl; N-(heteroaryl-$C_1$-$C_6$-alkyl)aminosulfonyl; phenyl-$C_1$-$C_3$-alkylsulfonyl; 5- to 8-membered heterocyclylsulfonyl; $C_1$-$C_6$-alkylsulfonyl; phenyl; optionally substituted phenyl substituted by one or more radicals selected from chloro, fluoro, bromo, methoxy, methylthio and methylthiosulfonyl; 5- to 9-membered heteroaryl; chloro substituted thienyl; phenyl-$C_1$-$C_6$-alkylcarbonyl; phenylcarbonyl; 4-chlorophenylcarbonyl; 4-hydroxyphenylcarbonyl; 4-trifluoromethylphenylcarbonyl; 4-methoxyphenylcarbonyl; aminocarbonyl; formyl; and $C_1$-$C_6$-alkylcarbonyl;

wherein the A ring atoms $A^1$, $A^2$, $A^3$ are carbon and $A^4$ is carbon or nitrogen, or wherein $R^2$ together with ring A forms a naphthyl, benzofurylphenyl, or quinolyl radical;

or an isomer thereof.

12. The pharmaceutical composition according to claim 2, wherein the third-generation coxib-compound is selected from the group consisting of 6-chloro-2-trifluoromethyl-2H-1-benzopyran-3-carboxylic acid;
6-chloro-7-methyl-2-trifluoromethyl-2H-1-benzopyran-3-carboxylic acid;
8-(1-methylethyl)-2-trifluoromethyl-2H-1-benzopyran-3-carboxylic acid;
6-chloro-7-(1,1-dimethylethyl)-2-trifluoromethyl-2H-1-benzopyran-3-carboxylic acid;
6-chloro-8-(1-methylethyl)-2-trifluoromethyl-2H-1-benzopyran-3-carboxylic acid;
2-trifluoromethyl-3H-naphthopyran-3-carboxylic acid;
7-(1,1-dimethylethyl)-2-trifluoromethyl-2H-1-benzopyran-3-carboxylic acid;
6-bromo-2-trifluoromethyl-2H-1-benzopyran-3-carboxylic acid;
8-chloro-2-trifluoromethyl-2H-1-benzopyran-3-carboxylic acid;
6-trifluoromethoxy-2-trifluoromethyl-2H-1-benzopyran-3-carboxylic acid;
5,7-dichloro-2-trifluoromethyl-2H-1-benzopyran-3-carboxylic acid;
8-phenyl-2-trifluoromethyl-2H-1-benzopyran-3-carboxylic acid;
7,8-dimethyl-2-trifluoromethyl-2H-1-benzopyran-3-carboxylic acid;
6,8-bis(dimethylethyl)-2-trifluoromethyl-2H-1-benzopyran-3-carboxylic acid;
7-(1-methylethyl)-2-trifluoromethyl-2H-1-benzopyran-3-carboxylic acid;
7-phenyl-2-trifluoromethyl-2H-1-benzopyran-3-carboxylic acid;
6-chloro-7-ethyl-2-trifluoromethyl-2H-1-benzopyran-3-carboxylic acid;
6-chloro-8-ethyl-2-trifluoromethyl-2H-1-benzopyran-3-carboxylic acid;
6-chloro-7-phenyl-2-trifluoromethyl-2H-1-benzopyran-3-carboxylic acid;
6,7-dichloro-2-trifluoromethyl-2H-1-benzopyran-3-carboxylic acid;
6,8-dichloro-2-trifluoromethyl-2H-1-benzopyran-3-carboxylic acid;
2-trifluoromethyl-3H-naphtho[2,1-b]pyran-3-carboxylic acid;
6-chloro-8-methyl-2-trifluoromethyl-2H-1-benzopyran-3-carboxylic acid;
8-chloro-6-methyl-2-trifluoromethyl-2H-1-benzopyran-3-carboxylic acid;
8-chloro-6-methoxy-2-trifluoromethyl-2H-1-benzopyran-3-carboxylic acid;
6-bromo-8-chloro-2-trifluoromethyl-2H-1-benzopyran-3-carboxylic acid;
8-bromo-6-fluoro-2-trifluoromethyl-2H-1-benzopyran-3-carboxylic acid;
8-bromo-6-methyl-2-trifluoromethyl-2H-1-benzopyran-3-carboxylic acid;
8-bromo-5-fluoro-2-trifluoromethyl-2H-1-benzopyran-3-carboxylic acid;
6-chloro-8-fluoro-2-trifluoromethyl-2H-1-benzopyran-3-carboxylic acid;
6-bromo-8-methoxy-2-trifluoromethyl-2H-1-benzopyran-3-carboxylic acid;
6-[[(phenylmethyl)amino]sulfonyl]-2-trifluoromethyl-2H-1-benzopyran-3-carboxylic acid;
6-[(dimethylamino)sulfonyl]-2-trifluoromethyl-2H-1-benzopyran-3-carboxylic acid;
6-[(methylamino)sulfonyl]-2-trifluoromethyl-2H-1-benzopyran-3-carboxylic acid;
6-[(4-morpholino)sulfonyl]-2-trifluoromethyl-2H-1-benzopyran-3-carboxylic acid;
6-[(1,1-dimethylethyl)aminosulfonyl]-2-trifluoromethyl-2H-1-benzopyran-3-carboxylic acid;
6-[(2-methylpropyl)aminosulfonyl]-2-trifluoromethyl-2H-1-benzopyran-3-carboxylic acid;
6-methylsulfonyl-2-trifluoromethyl-2H-1-benzopyran-3-carboxylic acid;
8-chloro-6-[[(phenylmethyl)amino]sulfonyl]-2-trifluoromethyl-2H-1-benzopyran-3-carboxylic acid;
6-phenylacetyl-2-trifluoromethyl-2H-1-benzopyran-3-carboxylic acid;
6,8-dibromo-2-trifluoromethyl-2H-1-benzopyran-3-carboxylic acid;
8-chloro-5,6-dimethyl-2-trifluoromethyl-2H-1-benzopyran-3-carboxylic acid;
6,8-dichloro-(S)-2-trifluoromethyl-2H-1-benzopyran-3-carboxylic acid;
6-benzylsulfonyl-2-trifluoromethyl-2H-1-benzopyran-3-carboxylic acid;
6-[[N-(2-furylmethyl)amino]sulfonyl]-2-trifluoromethyl-2H-1-benzopyran-3-carboxylic acid;
6-[[N-(2-phenylethyl)amino]sulfonyl]-2-trifluoromethyl-2H-1-benzopyran-3-carboxylic acid;
6-iodo-2-trifluoromethyl-2H-1-benzopyran-3-carboxylic acid;
7-(1,1-dimethylethyl)-2-pentafluoroethyl-2H-1-benzopyran-3-carboxylic acid; and
6-chloro-2-trifluoromethyl-2H-1-benzothiopyran-3-carboxylic acid;

or an isomer thereof.

13. The pharmaceutical composition according to claim 3, wherein the third-generation coxib-compound is selected from the group consisting of 6-chloro-2-trifluoromethyl-2H-1-benzopyran-3-carboxylic acid;
6-chloro-7-methyl-2-trifluoromethyl-2H-1-benzopyran-3-carboxylic acid;
8-(1-methylethyl)-2-trifluoromethyl-2H-1-benzopyran-3-carboxylic acid;
6-chloro-7-(1,1-dimethylethyl)-2-trifluoromethyl-2H-1-benzopyran-3-carboxylic acid;
6-chloro-8-(1-methylethyl)-2-trifluoromethyl-2H-1-benzopyran-3-carboxylic acid;
2-trifluoromethyl-3H-naphthopyran-3-carboxylic acid;
7-(1,1-dimethylethyl)-2-trifluoromethyl-2H-1-benzopyran-3-carboxylic acid;
6-bromo-2-trifluoromethyl-2H-1-benzopyran-3-carboxylic acid;
8-chloro-2-trifluoromethyl-2H-1-benzopyran-3-carboxylic acid;
6-trifluoromethoxy-2-trifluoromethyl-2H-1-benzopyran-3-carboxylic acid;
5,7-dichloro-2-trifluoromethyl-2H-1-benzopyran-3-carboxylic acid;
8-phenyl-2-trifluoromethyl-2H-1-benzopyran-3-carboxylic acid;
7,8-dimethyl-2-trifluoromethyl-2H-1-benzopyran-3-carboxylic acid;

6,8-bis(dimethylethyl)-2-trifluoromethyl-2H-1-benzopyran-3-carboxylic acid;
7-(1-methylethyl)-2-trifluoromethyl-2H-1-benzopyran-3-carboxylic acid;
7-phenyl-2-trifluoromethyl-2H-1-benzopyran-3-carboxylic acid;
6-chloro-7-ethyl-2-trifluoromethyl-2H-1-benzopyran-3-carboxylic acid;
6-chloro-8-ethyl-2-trifluoromethyl-2H-1-benzopyran-3-carboxylic acid;
6-chloro-7-phenyl-2-trifluoromethyl-2H-1-benzopyran-3-carboxylic acid;
6,7-dichloro-2-trifluoromethyl-2H-1-benzopyran-3-carboxylic acid;
6,8-dichloro-2-trifluoromethyl-2H-1-benzopyran-3-carboxylic acid;
2-trifluoromethyl-3H-naphtho[2,1-b]pyran-3-carboxylic acid;
6-chloro-8-methyl-2-trifluoromethyl-2H-1-benzopyran-3-carboxylic acid;
8-chloro-6-methyl-2-trifluoromethyl-2H-1-benzopyran-3-carboxylic acid;
8-chloro-6-methoxy-2-trifluoromethyl-2H-1-benzopyran-3-carboxylic acid;
6-bromo-8-chloro-2-trifluoromethyl-2H-1-benzopyran-3-carboxylic acid;
8-bromo-6-fluoro-2-trifluoromethyl-2H-1-benzopyran-3-carboxylic acid;
8-bromo-6-methyl-2-trifluoromethyl-2H-1-benzopyran-3-carboxylic acid;
8-bromo-5-fluoro-2-trifluoromethyl-2H-1-benzopyran-3-carboxylic acid;
6-chloro-8-fluoro-2-trifluoromethyl-2H-1-benzopyran-3-carboxylic acid;
6-bromo-8-methoxy-2-trifluoromethyl-2H-1-benzopyran-3-carboxylic acid;
6-[[(phenylmethyl)amino]sulfonyl]-2-trifluoromethyl-2H-1-benzopyran-3-carboxylic acid;
6-[(dimethylamino)sulfonyl]-2-trifluoromethyl-2H-1-benzopyran-3-carboxylic acid;
6-[(methylamino)sulfonyl]-2-trifluoromethyl-2H-1-benzopyran-3-carboxylic acid;
6-[(4-morpholino)sulfonyl]-2-trifluoromethyl-2H-1-benzopyran-3-carboxylic acid;
6-[(1,1-dimethylethyl)aminosulfonyl]-2-trifluoromethyl-2H-1-benzopyran-3-carboxylic acid;
6-[(2-methylpropyl)aminosulfonyl]-2-trifluoromethyl-2H-1-benzopyran-3-carboxylic acid;
6-methylsulfonyl-2-trifluoromethyl-2H-1-benzopyran-3-carboxylic acid;
8-chloro-6-[[(phenylmethyl)amino]sulfonyl]-2-trifluoromethyl-2H-1-benzopyran-3-carboxylic acid;
6-phenylacetyl-2-trifluoromethyl-2H-1-benzopyran-3-carboxylic acid;
6,8-dibromo-2-trifluoromethyl-2H-1-benzopyran-3-carboxylic acid;
8-chloro-5,6-dimethyl-2-trifluoromethyl-2H-1-benzopyran-3-carboxylic acid;
6,8-dichloro-(S)-2-trifluoromethyl-2H-1-benzopyran-3-carboxylic acid;
6-benzylsulfonyl-2-trifluoromethyl-2H-1-benzopyran-3-carboxylic acid;
6-[[N-(2-furylmethyl)amino]sulfonyl]-2-trifluoromethyl-2H-1-benzopyran-3-carboxylic acid;
6-[[N-(2-phenylethyl)amino]sulfonyl]-2-trifluoromethyl-2H-1-benzopyran-3-carboxylic acid;
6-iodo-2-trifluoromethyl-2H-1-benzopyran-3-carboxylic acid;
7-(1,1-dimethylethyl)-2-pentafluoroethyl-2H-1-benzopyran-3-carboxylic acid; and
6-chloro-2-trifluoromethyl-2H-1-benzothiopyran-3-carboxylic acid;
or an isomer thereof.

14. The pharmaceutical composition according to claim 2, wherein the third-generation coxib-compound is selected from the group consisting of
6-nitro-2-trifluoromethyl-2H-1-benzopyran-3-carboxylic acid;
6-chloro-8-methyl-2-trifluoromethyl-2H-1-benzopyran-3-carboxylic acid;
(S)-6-chloro-7-(1,1-dimethylethyl)-2-trifluoromethyl-2H-1-benzopyran-3-carboxylic acid;
2-trifluoromethyl-2H-naphtho[2,3-b]pyran-3-carboxylic acid;
6-chloro-7-(4-nitrophenoxy)-2-trifluoromethyl-2H-1-benzopyran-3-carboxylic acid;
(S)-6,8-dichloro-2-trifluoromethyl-2H-1-benzopyran-3-carboxylic acid;
6-chloro-2-trifluoromethyl-4-phenyl-2H-1-benzopyran-3-carboxylic acid;
6-(4-hydroxybenzoyl)-2-trifluoromethyl-2H-1-benzopyran-3-carboxylic acid;
2-(trifluoromethyl)-6-[(trifluoromethyl)thio]-2H-1-benzothiopyran-3-carboxylic acid;
6,8-dichloro-2-trifluoromethyl-2H-1-benzothiopyran-3-carboxylic acid;
6-(1,1-dimethylethyl)-2-trifluoromethyl-2H-1-benzothiopyran-3-carboxylic acid;
6,7-difluoro-1,2-dihydro-2-trifluoromethyl-3-quinolinecarboxylic acid;
6-chloro-1,2-dihydro-1-methyl-2-trifluoromethyl-3-quinolinecarboxylic acid;
6-chloro-2-trifluoromethyl-1,2-dihydro[1,8]naphthyridin-3-carboxylic acid; and
(S)-6-chloro-1,2-dihydro-2-trifluoromethyl-3-quinolinecarboxylic acid;
or an isomer thereof.

15. The pharmaceutical composition according to claim 3, wherein the third-generation coxib-compound is selected from the group consisting of
6-nitro-2-trifluoromethyl-2H-1-benzopyran-3-carboxylic acid;
6-chloro-8-methyl-2-trifluoromethyl-2H-1-benzopyran-3-carboxylic acid;
(S)-6-chloro-7-(1,1-dimethylethyl)-2-trifluoromethyl-2H-1-benzopyran-3-carboxylic acid;
2-trifluoromethyl-2H-naphtho[2,3-b]pyran-3-carboxylic acid;
6-chloro-7-(4-nitrophenoxy)-2-trifluoromethyl-2H-1-benzopyran-3-carboxylic acid;
(S)-6,8-dichloro-2-trifluoromethyl-2H-1-benzopyran-3-carboxylic acid;
6-chloro-2-trifluoromethyl-4-phenyl-2H-1-benzopyran-3-carboxylic acid;
6-(4-hydroxybenzoyl)-2-trifluoromethyl-2H-1-benzopyran-3-carboxylic acid;
2-(trifluoromethyl)-6-[(trifluoromethyl)thio]-2H-1-benzothiopyran-3-carboxylic acid;
6,8-dichloro-2-trifluoromethyl-2H-1-benzothiopyran-3-carboxylic acid;
6-(1,1-dimethylethyl)-2-trifluoromethyl-2H-1-benzothiopyran-3-carboxylic acid;

6,7-difluoro-1,2-dihydro-2-trifluoromethyl-3-quinolinecarboxylic acid;

6-chloro-1,2-dihydro-1-methyl-2-trifluoromethyl-3-quinolinecarboxylic acid;

6-chloro-2-trifluoromethyl-1,2-dihydro[1,8]naphthyridin-3-carboxylic acid; and (S)-6-chloro-1,2-dihydro-2-trifluoromethyl-3-quinolinecarboxylic acid;

or an isomer thereof.

16. The pharmaceutical composition according to claim 2, wherein the basic amine or the basic amino acid is tromethamine, triethanolamine, diethanolamine, monoethanolamine, glucosamine, galactosamine, fructosamine, meglumine, N-ethyl glucamine, lysine, arginine, histidine, tryptophan or ornithine; and the cyclodextrin is β-cyclodextrin, hydroxypropyl-β-cyclodextrin, or sodium sulfobutylether-β-cyclodextrin (SBECD).

17. The pharmaceutical composition according to claim 3, wherein the basic amine or the basic amino acid is tromethamine, triethanolamine, diethanolamine, monoethanolamine, glucosamine, galactosamine, fructosamine, meglumine, N-ethyl glucamine, lysine, arginine, histidine, tryptophan or ornithine; and the cyclodextrin is β-cyclodextrin, hydroxypropyl-β-cyclodextrin, or sodium sulfobutylether-β-cyclodextrin (SBECD).

18. The pharmaceutical composition according to claim 4, wherein the basic amine or the basic amino acid is tromethamine, triethanolamine, diethanolamine, monoethanolamine, glucosamine, galactosamine, fructosamine, meglumine, N-ethyl glucamine, lysine, arginine, histidine, tryptophan or ornithine; and the cyclodextrin is β-cyclodextrin, hydroxypropyl-β-cyclodextrin, or sodium sulfobutylether-β-cyclodextrin (SBECD).

* * * * *

UNITED STATES PATENT AND TRADEMARK OFFICE
CERTIFICATE OF CORRECTION

PATENT NO.        : 9,447,065 B2
APPLICATION NO.   : 14/351190
DATED             : September 20, 2016
INVENTOR(S)       : Iwata et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 263 days.

Signed and Sealed this
Twenty-fifth Day of September, 2018

Andrei Iancu
*Director of the United States Patent and Trademark Office*